US006469030B2

(12) United States Patent
Farrar et al.

(10) Patent No.: US 6,469,030 B2
(45) Date of Patent: Oct. 22, 2002

(54) METHODS FOR THE TREATMENT AND PREVENTION OF ILEUS

(75) Inventors: John J. Farrar, Chester Springs; Peter J. Schied, Southampton, both of PA (US); William K. Schmidt, Newark, DE (US); Randall L. Carpenter, Waban, MA (US)

(73) Assignee: Adolor Corporation, Exton, PA (US)

( * ) Notice: Subject to any disclaimer, the term of this patent is extended or adjusted under 35 U.S.C. 154(b) by 0 days.

(21) Appl. No.: 09/725,708

(22) Filed: Nov. 29, 2000

(65) Prior Publication Data

US 2001/0036951 A1 Nov. 1, 2001

Related U.S. Application Data

(63) Continuation-in-part of application No. 09/450,920, filed on Nov. 29, 1999, now abandoned.

(51) Int. Cl.$^7$ ............................................. A61K 31/451
(52) U.S. Cl. ........................................................ 514/331
(58) Field of Search ............................................ 514/331

(56) References Cited

U.S. PATENT DOCUMENTS

| 3,723,440 A | 3/1973 | Freter et al. ............ 260/293.54 |
|---|---|---|
| 4,115,400 A | 9/1978 | Zimmerman ......... 260/326.5 B |
| 4,176,186 A | 11/1979 | Goldbert et al. ............. 424/260 |
| 4,581,456 A | 4/1986 | Barnett ........................ 546/185 |
| 4,719,215 A | 1/1988 | Goldberg ..................... 514/282 |
| 4,730,048 A | 3/1988 | Portoghese ................... 546/45 |
| 4,769,367 A | 9/1988 | Cherry et al. ................ 514/217 |
| 4,769,372 A | 9/1988 | Kreek .......................... 514/282 |
| 4,774,230 A | 9/1988 | Tuttle et al. ................... 514/27 |
| 4,785,000 A | 11/1988 | Kreek et al. ................. 514/282 |
| 4,806,556 A | 2/1989 | Portoghese ................... 546/44 |
| 4,861,781 A | 8/1989 | Goldberg ..................... 514/282 |
| 4,880,801 A | 11/1989 | Kitchin et al. ............... 514/215 |
| 4,891,379 A | 1/1990 | Zimmerman et al. ........ 514/315 |
| 4,910,193 A | 3/1990 | Buchheit ...................... 514/216 |
| 4,920,102 A | 4/1990 | Gidda et al. ................... 514/28 |
| 4,987,136 A | 1/1991 | Kreek et al. ................. 514/282 |
| 4,992,450 A | 2/1991 | Zimmerman et al. ........ 514/315 |
| 5,064,834 A | 11/1991 | Zimmerman et al. ........ 514/279 |
| 5,102,887 A | 4/1992 | Goldberg ..................... 514/282 |
| 5,136,040 A | 8/1992 | Werner ........................ 546/218 |
| 5,140,023 A | 8/1992 | Becker et al. ................ 514/214 |
| 5,159,081 A | 10/1992 | Cantrell et al. .............. 546/226 |
| 5,250,542 A | 10/1993 | Cantrell et al. .............. 514/315 |
| 5,270,328 A | 12/1993 | Cantrell et al. .............. 514/331 |
| 5,280,294 A | 1/1994 | Flynn ........................... 514/294 |
| 5,319,087 A | 6/1994 | Zimmerman et al. ........ 546/240 |
| 5,362,756 A | 11/1994 | Riviere et al. ............... 514/651 |
| 5,382,591 A | 1/1995 | Barberich et al. ........... 514/413 |
| 5,411,745 A | 5/1995 | Oshlack et al. .............. 424/456 |
| 5,422,356 A | 6/1995 | Zimmerman et al. ........ 514/317 |
| 5,434,171 A | 7/1995 | Frank et al. ................. 514/331 |
| 5,460,826 A | 10/1995 | Merrill et al. ............... 424/470 |
| 5,498,718 A | 3/1996 | Werner ........................ 546/348 |
| RE35,218 E | 4/1996 | Becker et al. ............... 514/214 |
| 5,520,931 A | 5/1996 | Persson et al. .............. 424/473 |
| 5,593,695 A | 1/1997 | Merrill et al. ............... 424/480 |
| 5,736,550 A | 4/1998 | Kikuchi et al. .............. 514/261 |
| 5,753,654 A | 5/1998 | Kikuchi et aL. .......... 514/230.5 |
| 5,767,083 A | 6/1998 | Abajian et al. ................ 514/16 |
| 5,795,861 A | 8/1998 | Kolterman et al. ............ 514/12 |
| 5,811,451 A | 9/1998 | Minoia et al. ............... 514/443 |
| 5,861,014 A | 1/1999 | Familoni ....................... 607/40 |
| 5,879,705 A | 3/1999 | Heafield et al. ............. 424/464 |
| 5,888,529 A | 3/1999 | Bunnett et al. .............. 424/422 |
| 5,968,551 A | 10/1999 | Oshlack et al. ............. 424/456 |
| 5,972,954 A | 10/1999 | Foss et al. ................... 514/282 |
| 5,972,962 A | 10/1999 | Belfield et al. .............. 514/315 |

FOREIGN PATENT DOCUMENTS

| AU | 9176319 | 11/1992 |
|---|---|---|
| EP | 506478 | 9/1992 |
| JP | 1068376 | 3/1989 |
| WO | WO 98/25613 | 6/1998 |
| WO | WO 99/22737 | 5/1999 |

OTHER PUBLICATIONS

Macfadyen, A.J., et al., "Pain management in the pediatric intensive care unit," *Critical Care Clinics, Pain Management*, 1999, 15(1), 185–200.

McArdle, P., et al., "Intravenous analgesia," *Critical Care Clinics, Pain Management*, 1999, 15(1), 89–104.

Osol, A. et al. (Eds.), "Analgesics and Antipyretics," *Remington's Pharmaceutical Sciences*, 15$^{th}$ Ed., under section entitled Opiate Analgesics, 1975, p. 1098.

Windholz, M., et al. (Eds.), of The Merck Index, *An Encyclopedia of Chemicals, Drugs, and Biologicals*, 10$^{th}$ Ed., 1983, No. 2423, p. 350.

"Cancer pain remedy wins orphan drug status," *Oncology*, 1880, 10(12) (Dec., 1996).

Amin, H.M. et al., "Efficacy of methylnaltrexone versus naloxone for reversal of morphine–induced depression of hypoxic ventilatory response," *Anesth. Analog.*, 1994, 78(4), 701–705 (abstract only).

Amir, S. et al., "Endorphins in endotoxin–induced hyperglycemia in mice," *Arch. Toxicol. Suppl.*, 1983, 6, 261–265 (abstract only).

Argentieri, T.M., et al., "Interaction of the opiate antagonist, naltrexone methyl bromide, with the acetylcholine receptor system of the motor end–plate," *Brain Res. (Netherlands)*, 1983, 277(2), 377–379 (abstract only).

Bado, A., et al., "Endogenous opioid peptides in the control of food intake in cats," *Peptides (United States)*, 1989, 10(5), 967–971 (abstract only).

(List continued on next page.)

*Primary Examiner*—Phyllis G. Spivack
(74) *Attorney, Agent, or Firm*—Woodcock Washburn LLP

(57) ABSTRACT

Methods for the treatment and/or prevention of ileus are disclosed. The methods comprise administering to a patient an effective amount of a peripheral mu opioid antagonist compound. Preferred compounds for use in the methods include piperidine-N-alkylcarboxylates.

26 Claims, 3 Drawing Sheets

OTHER PUBLICATIONS

Bagnol, D., et al., "Cellular Localization and Distribution of the Cloned Mu and Kappa Opioid Receptors in Rat Gastrointestinal Tract," *Neuroscience,* 1997, 81(2), 579–591.

Bagnol, D., et al., "Changes in enkephalin immunoreactivity of sympathetic ganglia and digestive tract of the cat after splanchnic nerve ligation" *Regul. Pept.* 1993, 47(3), 259–273.

Bansinath, M., et al., "Evidence for a peripheral action of thyrotropin releasing hormone on gastrointestinal transit in mice," *Neuropharmacology,* 1988, 27(4), 433–437 (abstract only).

Baratti, C.M., "The impairment of retention induced by pentylenetetrazol in mice may be mediated by a release of opioid peptides in the brain," *Behav. Neural Biol.* (*United States*), 1987, 48(2), 183–196 (abstract only).

Bechara, A., et al., "Peripheral receptors mediate the aversive conditioning effects of morphine in the rat," *Pharm. Biochem. Behav.* (*United States*), 1987, 28(2), 219–225 (abstract only).

Bechara, A., et al., "The tegmental pedunculopontine nucleus: a brain–stem output of the limbic system critical for the conditioned place preferences produced by morphine and amphetamine," *J. Neurosci* (*United States*), 1989, 9(10), 3400–3409 (abstract only).

Bechara A., et al., "Opposite motivational effects of endogenous opioids in brain and periphery," *Nature* (*England*), 1985, 314(6011), 533–534 (abstract only).

Berde, C.B., et al., "Peripheral, Spinal, and Supraspinal Targets of Opioids and NSAIDs," *IASP Newsletter,* 1996, 1–8.

Bergasa, N.V., et al., "Management of the pruritus of cholestasis: potential role of opiate antagonists," *Am. J. Gastroenterol,* 1991, 86(10), 1404–1412.

Bhargava, H.N. et al., "Effect of nitric oxide synthase inhibition on tolerance to the analgesic action of D–Pen$^2$, D–Pen$^5$ enkephalin and morphine in the mouse," *Neuropeptides,* 1996, 30(3), 219–223.

Bianchetti, A., et al., "Relative affinities of the quaternary narcotic antagonist, N–methyl levallorphan (SR 58002), for different types of opioid receptors" *Neuropeptides,* 1985, 5(4–6), 379–382 (abstract only).

Bianchetti, A., et al., "Pharmacological actions of levallorphan allyl bromide (CM 32191), a new peripheral narcotic antagonist" *Life Sci,* 31(20–21), 2261–2264 (abstract only).

Bianchi, G., et al., "The peripheral narcotic antagonist N–allyl levallorphan–bromide (CM 32191) selectively prevents morphine antipropulsive action and buprenorphine in–vivo binding in the rat intestine," *J. Pharm. Pharmacol,* 1984, 36(5), 326–330 (abstract only).

Bilsky, E.J., et al., "Effects of Naloxone and D–Phe–Cys–Tyr–D–Trp–Arg–Thr–Pen–Thr–NH$_2$ and the protein kinase inhibitors H7 and H8 on acute morphine dependence and antinociceptive tolerance in mice," *J. Pharmacol. Exp. Ther.,* 1996, 277, 484–490.

Blank, M.S., et al., "Central, stereoselective receptors mediate the acute effects of opiate antagonists on luteinizing hormone secretion," *Life Sci.* (*England*), 1986, 39(17), 1493–1499 (abstract only).

Brown, D.R. et al., "The Use of Quaternary Narcotic Antagonists in Opiate Research," *Neuropharmacology,* 1985, 24(3), 181–191.

Brown, D.R., et al., "Reversal of Morpine–Induced Catalepsy in the Rat by Narcotic Antagonists and Their Quaternary Derivatives," *Neuropharmacology,* 1983, 22(3A), 317–321.

Brown, D.R., et al., "Opiate antagonists: central sites of action in suppressing water intake of the rat," *Brain Res.,* 1981, 221(2), 432–436 (abstract only).

Calcagnetti, D.J., et al., "Central and peripheral injection of quaternary antagonist, SR58002C, reduces drinking" *Physiol. Behav.,* 1987, 40(5), 573–575 (abstract only).

Calcagnetti, D.J., et al., "Quaternary naltrexone reveals the central mediation of conditional opioid analgesia," *Pharma. Biochem. Behav.* (*United States*), 1987, 27(3), 529–531 (abstract only).

Caldwell, R.W., et al., "Actions of the opioid antagonist, nalmefene, and congeners on reperfusion cardiac arrhythmias and regional left coronary blood flow," *Pharmacology,* 1990, 41(3), 161–166 (abstract only).

Carr, K.D., et al., "Effects of naloxone and its quarternary analogue on stimulation–induced feeding," *Neuropharmacology* (*England*), 1983, 22(1), 127–130 (abstract only).

Corrigall, W.A., et al., "An analysis of the paradoxical effect of morphine on runway speed and food consumption," *Psychopharmacology,* 1986, 89(3), 327–333 (abstract only).

Corrigall, W.A., "Heroin self–administration: effects of antagonist treatment in lateral hypothalamus," *Pharmacol. Biochem. Behav.,* 1987, 27(4), 693–700 (abstract only).

Corrigall, W.A., et al., "Antagonist treatment in nucleus accumbens or periaqueductal grey affects heroin self–administration," *Pharmacol. Biochem. Behav.,* 1988, 30(2), 443–450 (abstract only).

Culpepper–Morgan, J.A., et al., "Treatment of opioid–induced constipation with oral naloxone: A pilot study," *Clin. Pharmacol. Ther.,* 1992, 90–95.

De Winter, Benedicte, et al., "Differential effect of indomethacin and ketorolac on postoperative ileus in rats," *Eur. J. Pharmacol,* 1998, 344, 71–76.

Dickson, P.R., et al., "GRF–induced feeding: evidence for protein selectivity and opiate involvement," *Peptides,* 1994, 15(8), 1343–1352 (abstract only).

*Dorland's Illustrated Medical Dictionary,* 24$^{th}$ ed., W.B. Saunders Company, Philadelphia 1965, 724.

*Dorland's Illustrated Medical Dictionary,* 27th ed., W.B. Saunders Company, Philadelphia 1998, 816.

*Dorland's Illustrated Medical Dictionary,* 27th ed., W.B. Saunders Company, Philadlephia 1988, 375.

Dourish, C.T., et al., "Enhancement of morphine analgesia and prevention of morphine tolerance in the rat by the cholecystokinin antagonist L–364, 718," *Eur. J. Pharmacol,* 1988, 147, 469–472.

Dragonetti, M., et al., "Levallorphan methyl iodide (SR 58002), a potent narcotic antagonist with peripheral selectivity superior to that of other quaternary compounds", *Life Sci.,* 1873, 33, Suppl. 1, 477–480 (abstract only).

Ellis, J.E., et al., "Premedication with oral and transdermal clonidine provides safe and efficacious postoperative sympatholysis," *Anesth. Analog.,* 1994, 79(6), 1133–1140 (abstract only).

Ferraz, Alvaro, A.B., M.D., et al., "Nonopioid Analgesics Shorten the Duration of Postoperative Ileus," *Dept. of Surgery and Physiology and Surgical Research Service,* 1995, vol. 61, 1079–1083.

Fletcher, P.J., "Opiate antagonists inhibit feeding induced by 8–OH–DPAT: possible mediation in the nucleus accumbens," *Brain Res.,* 1991, 560(1–2), 260–267 (abstract only).

Foss, J.F., et al., "Peripheral Antagonism of the Emetic Effect of Morphine by Methylnaltrexone," *Clinical Res.,* 1989, 37(2), 595A (abstract only).

Foss, J.F., et al., "Dose–Related Antagonism of the Emetic Effect of Morphine by Methylnaltrexone in Dogs," *J. Clin. Pharmacol.,* 1993, 33, 747–751.

Foss, J.F., "Excretion of Methylnaltrexone After a Single Oral Dose of the Compound," *National Center for Research Resouces,* 1999, 1 page (summary only).

Foss, J.F., et al., "Safety and tolerance of methylnaltrexone in healthy humans: a randomized, placebo–controlled, intravenous, ascending–dose, pharmacokinetic study," *J. Clin. Pharmacol.,* 1997, 37(1), 25–30 (abstract only).

Foss, J.F., et al., "Effects of methylnaltrexone on morphine–induced cough suppression in guinea pigs," *Life Sci.,* 1996, 59(15), 235–238 (abstract only).

Fotherby, F.J., et al., "Idiopathic slow–transit constipation: whole gut transittimes, measured by a new simplified method, are not shortened by opioid antagonists," *Aliment Pharmacol Ther.,* 1987, 1(4), 331–338.

Fox, D.A., et al., "Roles of central and peripheral mu, delta and kappa opioid receptors in the mediation of gastric acid secretory effects in the rat," *Dept. Pharma.,* 1988, 244(2), 456–462 (abstract only).

France, C.P., et al., "Comparison of naltrexone and quaternary naltrexone after systemic and intracereboventricular administration in pigeons," *Neuropharmacology (England),* 1987, 26(6), 541–548 (abstract only).

Friese, N., et al., "Reversal by K–Agonists of Peritoneal Irritation–Induced Ileus and Visceral Pain in Rats," *Life Sciences,* 1997, vol. 60(9), 625–634.

Hocking, M.P., "The effect of opioid receptor antagonist on postoperative ileus," *Dept. Vet. Affairs,* 1996 (abstract only).

Howd, R.A., et al., "Naloxone and Intestinal Motility," *SR Internationa, Life Sciences Division,* 1978, 34(10), 1310–1311.

Introini, I.B., et al., "Pharmacological evidence of a central effect of naltrexone, morphine, and beta–endorphin and a peripheral effect of met– and leu–enkephalin on retention of an inhibitory response in mice," *Behav. Neural. Biol. (United States),* 1985, 44(3), 434–436 (abstract only).

Jalowiec, J.E., "Suppression of juvenile social behavior requires antagonism of central opioid systems," *Pharmacol Biochem Behav. (United States),* 1989, 33(3), 697–700 (abstract only).

Kalivas, P.W., et al., "Enkephalin release into the ventral tegmental area in response to stress: modulation of mesocorticolimbic dopamine," *Brain Res. (Netherlands),* 1987, 414(2), 339–348 (abstract only).

Kam, P.C., et al., "Pruritus—itching for a cause and relief?" *Anaesthesia,* 1996, 51(12), 1133–1138 (abstract only).

Kapusta, D.R., et al., "Opioids in the systemic hemodynamic and renal responses to stress in spontaneously hypertensive rats," *Hypertension (United States),* 1989, 13(6 Pt. 2), 808–816 (abstract only).

Kastin, A.J., et al., "EEG evidence that morphine and an enkephalin analog cross the blood–drain barrier," *Pharmacol. Biochem. Behav.,* 1991, 40(4), 771–774 (abstract only).

Kelley, Mark C., et al., "Ketorolac Prevents Postoperative Small Intestinal Ileus in Rats," *American Journal of Surgery,* 1993, vol. 165, 107–112.

Kelly, S.J., et al., "Role of peripheral and central opioid activity in analgesia induced by restraint stress," *Life Sci. (England),* 1987, 41(6), 789–794 (abstract).

Koch, T.R., et al., "Inhibitory neuropeptides and intrinsic inhibitory innervation of descending human colon," *Digest. Dis. Sci.,* 1991, 36(6), 712–728 (abstract only).

Koob, G.F., et al., "Effects of opiate antagonists and their quaternary derivatives on heroin self–administration in the rat," *J. Pharmacol Exp. Ther. (United States),* 1984, 229(2), 481–486 (abstract only).

Kotake, A.M., et al., "Variations in Demethylation of N–methylnaltrexone in Mice, rats, dogs, and humans," *Xenobiotica,* 1989, 19(11), 1247–1254 (abstract only).

Kreek, M.J., et al., "Naloxone, A Specific Opioid Antagonist, Reverses Chronic Idiopathic Constipation," *Lancet,* 1983, 1(8319), 261–262.

Kuhn, F.J., et al., "Study on novel morphine antagonists in the animal experiment," *Arzneimittelforschung,* 1976, 26(11), 2009–2014 (abstract only).

Latasch, L., et al., "Aufhebung einer Morphin–induzierten Obstipation durch orales Naloxon," *Anaesthesist,* 1997, 46, 191–194 (abstract).

Linseman, M.A., "Central vs. peripheral mediation of opioid effects on alcohol consumption in free–feeding rats," *Pharmacol Biochem. Behav. (United States),* 1989, 33(2), 407–413 (abstract only).

Linseman, M.A., et al., "Effects of opioids on the absorption of alcohol," *Pharmacol Biochem Behav. (United States),* 1997, 58(1), 79–84 (abstract only).

Livingston, E.H., et al., "Postoperative Ileus," *Dig. Dis. Sci.,* 1990, 35(1), 121–132.

Locke, K.W., et al., "Characterization of the discriminative stimulus effects of centrally administered morphine in the rat," *Psychopharmacology (Berl.)(W. Germany),* 1985, 87(1), 1–6 (abstract only).

Loew, G.H., "Molecular: The designer's goal is to eliminate adverse side effects," *Modern Drug Disc.,* 1999, 24–30.

Mack, D.J., et al., "Paralytic ileus: response to naloxone," *Br. J. Surg.,* 1989, 76(10), 1101.

Mao, M.J., et al., "Oral administration of dextromethorphan prevents the development of morphine tolerance and dependence in rats," *Pain,* 1996, 67, 361–368.

Marks–Kaufman, R., et al., "Central and peripheral contributions of endogenous opioid systems to nutrient selection in rats," *Psychopharmacology (Berl.) (W. Germany),* 1985, 85(4), 414–418 (abstract only).

Martin, G.M., et al., "Morphine preexposure attenuates the aversive properties of opiates without preexposure to the aversive properties," *Pharmacol Biochem. Behav. (United States),* 1988, 30(3), 687–692 (abstract only).

Mickley, G.A., et al., "Quaternary naltrexone reverses morphine–induced behaviors," *Physiol Behav. (United States),* 1985, 35(2), 249–253 (abstract only).

Misra A.L., et al., "Intravenous kinetics and metabolism of [15, 16–3H] naltrexonium methiodide in the rat," *J. Pharm. Pharmacol (England),* 1987, 39(3), 225–227 (abstract only).

Moerman, I., et al., "Evaluation of methylnaltrexone for the reduction of postoperative vomiting and mausea incidences," *Acta Anaesth.,* 1995, 46, 127–132.

Mucha, R.F., "Is the motivational effect of opiate withdrawal reflected by common somatic indices of precipitated withdrawal? A place conditioning study in the rat," *Brain Res. (Netherlands),* 1987, 418(2), 214–220 (abstract only).

Mucha, R.F., "Taste aversion involving central opioid antagonism is potentiated in morphine–dependent rats," *Life Sci.* (*England*), 1989, 45(8), 671–678 (abstract only).

Murphy, D.B., et al., "Opioid–induced delay in gastric emptying: a peripheral mechanism in humans," *Anesthesiology*, 1997, 87(4), 765–770 (abstract only).

Naranjo, J.R., et al., "Evidence for a central but not adrenal, opioid mediation in hypertension induced by brief isolation in the rat," *Life Sci.* (*England*), 1986, 38(21), 1923–1930 (abstract only).

Nichols, M.L. et al., "Enhancement of the antiallodynic and antinociceptive efficancy of spinal morphine by antisera to dynorphin A (1–13) or MK–801 in a nerve–ligation model of peripheral neuropathy," *Pain*, 1997, 69, 317–322.

Orchin, et al., *The Vocabulary of Organic Chemistry*, John Wiley and Sons Inc., 1980, 126.

Quock R.M., et al., "Narcotic antagonist–induced hypotension in the spontaneously hypertensive rate," *Life Sci.* (*England*), 1985, 37(9), 819–826 (abstract only).

Quock, R.M., et al., "Central pharmacological activity of a quaternary ammonium compound in streptozotocin diabetic mice," *Life Sci.* (*England*), 1988, 43(17), 1411–1417 (abstract only).

Quock, R.M., et al., "Influence of narcotic antagonist drugs upon nitrous oxide analgesia in mice," *Brain Res.* (*Netherlands*), 1988, 440(1), 35–41 (abstract only).

Rae, G.A., et al. "Methylnalorphinium fails to reverse naloxone–sensitive stress–induced analgesia in mice," *Pharmacol Biochem Behav.*, 1986, 24(4), 829–832 (abstract only).

Ramarao, P., "Evidence for the involvement of central opioidergic systems in L–tyrosine methyl esterinduced analgesia in the rat," *Pharmacology* (*Switzerland*), 1988, 37 (1), 1–7 (abstract only).

Ramabadran, K., "Effects of N–Methylnaloxane and N–Methylnaltrexone on Nociception and Precipitated Abstinence in Mice," *Life Sci.*, 1982, 31(12–13), 1253–1256.

Reisine, T., et al., "Opioid analgesics and antagonists," Hardman, J.G. et al., eds. And Goodman & Gilman's *The Pharmacological Basis of Therapeutics* Ninth Edition 1996, 521–555.

Resnick J., "Delayed Gastric Emptying and Postoperative Ileus after Nongastric Abdominal Surgery: Part II," *Am. J. Gastroenterology*, 1997, 92(6), 934–940.

Resnick, J., "Delayed Gastric Emptying and Postoperative Ileus after Nongastric Abdominal Surgery: Part I," *Am. J. Gastroenterology*, 1997, 92(5), 751–762.

Rivière, Pierre J.M., et al., "Fedotozine Reverses Ileus Induced by Surgery or Peritonitis: Action at Peripheral κ–Opioid Receptors," *Gastroenterology*, 1993, 104, 724–731.

Roger, T., "Colonic motor responses in the pony: relevance of colonic stimulation by opiate antagonists," *Am. J. Vet Res.*, 1985, 46(1), 31–35.

Rosow, C.E., "Methylnaltrexone: reversing the gastrointestinal effects of opioids," *Anesthesiology*, 1997, 87(4), 736–737.

Russell, James, et al., "Antagonism of Gut, but Not Central Effects of Morphine with Quaternary Narcotic Antagonists," *Eur. J. Pharmacol*, 1982, 78, 255–261 (abstract only).

Sbacchi M., et al., "Antagonism by N–methyl levallorphan-methane sulphonate (SR 58002 C) of morphine–elicited acute and chronic central and peripheral effects," *Life Sci.*, 1988, 42(21), 2079–2089 (abstract only).

Schang, J.C., et al., "Beneficial Effects of Naloxone in a Patient with Intestinal Pseudoobstruction," *Am. J. Gastroenerol.*, 1985, 80(6), 407–411.

Schmidhammer, et al., "30. Synthesis and Riological Evaluation of 14–Alkoxymorphinans"; "14–O–Ethyl–5–methylnaltrexone, an Opioid Antagonist with Unusual Selectrivity," *Helvetica Chimica Acta*, 1993, (76), 476–480.

Schuller, A.G.P., et al., "But Not Morphine, Inhibits GI Transit in Mu Opioid Receptor Deficient Mice," *Soc. Neurosci. Abstr.*, 1998, 24, 524.

Shaham, Y., et al., "Effects of restraint stress and intra–ventral tegmental area injections of morphine and methyl naltrexone on the discriminative stimulus effects of heroin in the rat," *Pharmacol Biochem. Behav.* (*United States*), 1995, 51(2–3), 491–498 (abstract only).

Solvason, H.B., et al., "Naltrexone blocks the expression of the conditioned elevation of natural killer cell activity in BALB/c mice," *Brain Behav. Immun.* (*United States*), 1989, 3(3), 247–262 (abstract only).

Sykes, N.P., "An investigation of the ability of oral naloxone to correct opioid–related constipation in patents with advanced cancer," *Palliative Medicine*, 1996, 10, 135–144.

*Taber's Cyclopedic Medical Dictionary*, F.A. Davis Company, Philadelphia, 15 ed., 1985, 824–825.

Tavani, A., et al., "Morphine no longer blocks gastrointestinal transit but retains antinociceptive action in diallylnormorphine–pretreated rats," *Eur. J. Pharmacol*, 1979, 59(1–2), 151–154 (abstract only).

Trujillo, K.A., et al., "Effects of opiate antagonists and their quaternary analogues on nucleus accumbens self–stimulation," *Behav. Brain Res.* (*Netherlands*), 1989, 181–188 (abstract only).

Vaccarino, F.J., et al., "Effects of opiate antagonist treatment into either the periaqueductal grey or nucleus accumbens on heroin–induced locomotor activation," *Brain Res. Bull.* (*United States*), 1987, 19 (5), 545–549 (abstract only).

Valentino, Rita J., et al., "Quaternary Naltrexone: Evidence for the Central Mediation of Discriminative Stimulus Effects of Narcotic Agonists and Antagonists," *CNS mediation of narcotic discrimination*, 1981, vol. 217(3), 652–659.

Valentino, Rita J., et al., "Receptor Binding, Antagonist, and Withdrawal Precipitating Properties of Opiate Antagonists," *Life Sciences*, 1983, vol. 32, 2887–2896.

van der Kooy, D., et al., "Hyperalgesia mediated by peripheral opiate receptors in the rat," *Behav. Brain Res*, 1985, 17(3), 203–211 (abstract only).

Vollmar A.M., et al., "The effect of opioids on rat plasma atrial natriuretic peptide," *Eur. J. Pharmacol* (*Netherlands*), 1987, 143(3), 315–321 (abstract only).

Wittert, G., et al., "Tissue Distribution of Opioid Receptor Gene Expression in the Rat," *Biochem. Biophys. Res. Commun.*, 1996, 218, 877–881.

Yuan, C.S., et al., "Efficacy of orally administered methylnaltrexone in decreasing subjective effects after intravenous morphine," *Drug Alcohol Dependence*, 1998, 52, 161–165.

Yuan, C.S., et al., "Methylnaltrexone for Reversal of Constipation Due to Chronic Methadone Use," *JAMA*, 2000, 283(3), 13 pages.

Yuan, C.S., et al., "Effects of intravenous methylnaltrexone on opioid–induced gut motility and transit time changes in subjects receiving chronic methadone therapy: a pilot study," *Pain*, 1999, 82, 1–5.

Yuan, C.S., et al., "Effects of methylnaltrexone on morphine–induced inhibition of contraction in isolated guinea–pig ileum and human intesting," *Eur. J. Pharmacol.,* 1995, 276(1–2), 107–111 (abstract included only).

Yuan, C.S., et al., "Methylnaltrexone Prevents Morphine–Induced Delay in Oral–Cecal Transit Time Without Affecting Analgesia: A Double–Blind Randomized Placebo-Controlled Trial," *Clin Pharmacol Ther.* (*United States*), 1996, 59(4), 469–475.

Yuan, C.S., et al., "The safety and efficacy of oral methylnaltrexone in preventing morphine–induced delay in oral–cecal transit time," *Clin Pharmacol Ther.* (*United States*), 1997, 61(4), 467–475 (abstract only).

Zimmerman, D.M., et al., "Discovery of a Potent, Peripherally Selective trans–3,4–Dimethyl–4–)3–hydroxyphenyl) piperidine Opioid Antagonist for the Treatment of Gastrointestinal Motility Disorders," *J. Med. Chem.,* 1994, 37, 2262–2265.

Zimmerman, D.M., et al., "LY246736 Dihydrate," *Drugs Future,* 1994, 19(12), 1078–1083.

METHODS FOR THE TREATMENT AND PREVENTION OF ILEUS

CROSS-REFERENCE TO RELATED APPLICATIONS

This application is a continuation-in-part of application Ser. No. 09/450,920, filed Nov. 29, 1999, now abandoned.

This application claims benefit under U.S.C. 119(e) to U.S. provisional application Ser. No. 60/287,560.

FIELD OF THE INVENTION

The present invention relates to novel methods for the treatment and prevention of ileus. More particularly, the present invention relates to novel methods for the treatment and prevention of ileus by using peripheral mu opioid antagonist compounds.

BACKGROUND OF THE INVENTION

It is well known that opioid drugs target three types of endogenous opioid receptors (i.e., mu, delta and kappa receptors) in biological systems. Many opiates, such as morphine, are mu opioid agonists that are often used as analgesics for the treatment of severe pain due to their activation of mu opioid receptors in the brain and central nervous system (CNS). Opioid receptors are, however, not limited to the CNS, and may be found in other tissues throughout the body. A number of side effects of opioid drugs may be caused by activation of these peripheral receptors. For example, administration of mu opioid agonists often results in intestinal dysfunction due to the large number of receptors in the wall of the gut (Wittert, G., Hope, P. and Pyle, D., *Biochemical and Biophysical Research Communications* 1996, 218, 877-881; Bagnol, D., Mansour, A., Akil, A. and Watson, S. J., *Neuroscience* 1997, 81, 579–591). Specifically, opioids are generally known to cause nausea and vomiting as well as inhibition of normal propulsive gastrointestinal function in animals and man (Reisine, T., and Pasternak, G., *Goodman & Gilman's The Pharmacological Basis of Therapeutics Ninth Edition* 1996, 521–555) resulting in side effects such as, for example, constipation.

Recent evidence has indicated that naturally occurring endogenous opioid compounds may also affect propulsive activity in the gastrointestinal (GI) tract. Met-enkephalin, which activates mu and delta receptors in both the brain and gut, is one of several neuropeptides found in the GI tract (Koch, T. R., Carney, J. A., Go, V. L., and Szurszewski, J. H., *Digestive Diseases and Sciences* 1991, 36, 712–728). Additionally, receptor knockout techniques have shown that mice lacking mu opioid receptors may have faster GI transit times than wild-type mice, suggesting that endogenous opioid peptides may tonically inhibit GI transit in normal mice (Schuller, A. G. P., King, M., Sherwood, A.C., Pintar, J. E., and Pasternak, G. W., *Society of Neuroscience Abstracts* 1998, 24, 524). Studies have shown that opioid peptides and receptors located throughout the GI tract may be involved in normal regulation of intestinal motility and mucosal transport of fluids in both animals and man (Reisine, T., and Pasternak, G., *Goodman & Gilman's The Pharmacological Basis of Therapeutics Ninth Edition* 1996, 521–555). Other studies show that the sympathetic nervous system may be associated with endogenous opioids and control of intestinal motility (Bagnol, D., Herbrecht, F., Jule, Y., Jarry, T., and Cupo, A., *Regul. Pept.* 1993, 47, 259–273). The presence of endogenous opioid compounds associated with the GI tract suggests that an abnormal physiological level of these compounds may lead to bowel dysfunction.

It is a common problem for patients having undergone surgical procedures, especially surgery of the abdomen, to suffer from a particular bowel dysfunction called post-surgical (or post-operative) ileus. "Ileus", as used herein, refers to the obstruction of the bowel or gut, especially the colon. See, e.g., *Dorland's Illustrated Medical Dictionary*, p. 816, 27th ed. (W.B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W.B. Saunders Company, Philadelphia 1988). Ileus may be diagnosed by the disruption of normal coordinated movements of the gut, resulting in failure of the propulsion of intestinal contents. See, e.g., Resnick, J. *Am. J. of Gastroenterology* 1997, 92, 751 and Resnick, J. *Am. J. of Gastroenterology*, 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, E. D. Jr. *Digestive Diseases and Sciences* 1990, 35, 121). Similarly, post-partum ileus is a common problem for women in the period following childbirth, and is thought to be caused by similar fluctuations in natural opioid levels as a result of birthing stress.

Gastrointestinal dysmotility associated with post-surgical ileus is generally most severe in the colon and typically lasts for 3 to 5 days. The administration of opioid analgesics to a patient after surgery may often contribute to bowel dysfunction, thereby delaying recovery of normal bowel function. Since virtually all patients receive opioid analgesics, such as morphine or other narcotics for pain relief after surgery, particularly major surgery, current post-surgical pain treatment may actually slow recovery of normal bowel function, resulting in a delay in hospital discharge and increasing the cost of medical care.

Post-surgical ileus may also occur in the absence of exogenous opioid agonists. It would be of benefit to inhibit the natural activity of endogenous opioids during and/or after periods of biological stress such as surgery and childbirth so that ileus and related forms of bowel dysfunction can be prevented or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased in addition to the benefit of minimizing patient discomfort. Thus, drugs which selectively act on opioid receptors in the gut would be ideal candidates for preventing and/or treating post-surgical and post-partum ileus. Of those, drugs that do not interfere with the effects of opioid analgesics in the CNS would be of special benefit in that they may be administered simultaneously for pain management with limited side effects.

Peripheral opioid antagonists that do not cross the blood-brain barrier into the CNS are known in the literature and have been tested in relation to their activity on the GI tract. In U.S. Pat. Nos. 5,250,542, 5,434,171, 5,159,081, and 5,270,328, peripherally selective piperidine-N-alkylcarboxylate opioid antagonists are described as being useful in the treatment of idiopathic constipation, irritable bowel syndrome and opioid-induced constipation. Also, U.S. Pat. No. 4,176,186 describes quaternary derivatives of noroxymorphone (i.e., methylnaltrexone) that are said to prevent or relieve the intestinal immobility side-effect of narcotic analgesics without reducing analgesic effectiveness. U.S. Pat. No. 5,972,954 describes the use of methylnaltrexone, enteric coated methylnaltrexone, or other quaternary derivatives of noroxymorphone for preventing and/or treating opioid- and/or nonopioid-induced side effects associated with opioid administration.

General opioid antagonists such as naloxone and naltrexone have also been implicated as being useful in the treatment of GI tract dysmotility. For example, U.S. Pat. No. 4,987,126 and Kreek, M. J. Schaefer, R. A., Hahn, E. F., Fishman, J. *Lancet* 1983, 1(8319), 261 disclose naloxone and other morphinan-based opioid antagonists (i.e., naloxone, naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G. *Am. J. Gastroenerol.* 1985, 80(6), 407). Furthermore, it has been implicated that naloxone may provide therapy for paralytic ileus (Mack, D. J. Fulton, J. D. *Br. J. Surg.* 1989, 76(10), 1101). However, it is well known that activity of naloxone and related drugs is not limited to peripheral systems and may interfere with the analgesic effects of opioid narcotics.

Inasmuch as post-surgical and post-partum ileus, for example, are common illnesses that add to the cost of health care and as yet have no specific treatments, there is a need for a specific and effective remedy. The majority of currently known opioid antagonist therapies are not peripherally selective and have the potential for undesirable side effects resulting from penetration into the CNS. Given the estimated 21 million inpatient surgeries and 26 outpatient surgeries each year, and an estimate of 4.7 million patients experiencing post-surgical ileus, methods involving opioid antagonists that are not only specific for peripheral systems, but specific for the gut, are desirable for treating post-surgical and post-partum ileus. The present invention is directed to this, as well as other important ends.

SUMMARY OF THE INVENTION

Accordingly, the present invention is directed, in part, to novel methods for treating and/or preventing ileus. Specifically, in one embodiment, there are provided novel methods of treating or preventing ileus comprising administering to a patient an effective amount of a compound of the following formula (I):

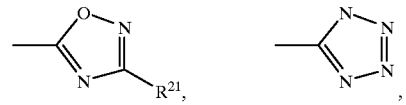

I wherein:
$R^1$ is hydrogen or alkyl;
$R^2$ is hydrogen, alkyl or alkenyl;
$R^3$ is hydrogen, alkyl, alkenyl, aryl, cycloalkyl, cycloalkenyl, cycloalkyl-substituted alkyl, cycloalkenyl-substituted alkyl or aryl-substituted alkyl;

$R^4$ is hydrogen, alkyl or alkenyl;
A is $OR^5$ or $NR^6R^7$; wherein:
$R^5$ is hydrogen, alkyl, alkenyl, cycloalkyl, cycloalkenyl, cycloalkyl-substituted alkyl, cycloalkenyl-substituted alkyl, or aryl-substituted alkyl;
$R^6$ is hydrogen or alkyl;
$R^7$ is hydrogen, alkyl, alkenyl, cycloalkyl, aryl, cycloalkyl-substituted alkyl, cycloalkenyl, cycloalkenyl-substituted alkyl, aryl-substituted alkyl, aryl-substituted alkyl, or alkylene substitued B or, together with the nitrogen atom to which they are attached, $R^6$ and $R^7$ form a heterocyclic ring;
B is

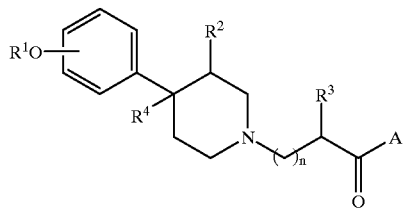

$C(=O)W$ or $NR^8R^9$; wherein;
$R^8$ is hydrogen or alkyl;
$R^9$ is hydrogen, alkyl, alkenyl, cycloalkyl-substituted alkyl, cycloalkyl, cycloalkenyl, cycloalkenyl-substituted alkyl, aryl or aryl-substituted alkyl or, together with the nitrogen atom to which they are attached, $R^8$ and $R^9$ form a heterocyclic ring;
W is $OR^{10}$, $NR^{11}R^{12}$, or OE; wherein
$R^{10}$ is hydrogen, alkyl, alkenyl, cycloalkyl, cycloalkenyl, cycloalkyl-substituted alkyl, cycloalkenyl-substituted alkyl, or aryl-substituted alkyl;
$R^{11}$ is hydrogen or alkyl;
$R^{12}$ is hydrogen, alkyl, alkenyl, aryl, cycloalkyl, cycloalkenyl, cycloalkyl-substituted alkyl, cycloalkenyl-substituted alkyl, aryl-substituted alkyl or alkylene substituted $C(=O)Y$ or, together with the nitrogen atom to which they are attached, $R^{11}$ and $R^{12}$ form a heterocyclic ring;
E is

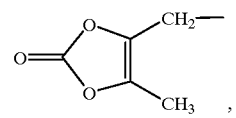

alkylene substituted $(C=O)D$, or $-R^{13}OC(=O)R^{14}$;
wherein
$R^{13}$ is alkyl substituted alkylene;
$R^{14}$ is alkyl;
D is $OR^{15}$ or $NR^{16}R^{17}$;
wherein:
$R^{15}$ is hydrogen, alkyl, alkenyl, cycloalkyl, cycloalkenyl, cycloalkyl-substituted alkyl, cycloalkenyl-substituted alkyl, or aryl-substituted alkyl;
$R^{16}$ is hydrogen, alkyl, alkenyl, aryl, aryl-substituted alkyl, cycloalkyl, cycloalkenyl, cycloalkyl-substituted alkyl or cycloalkenyl-substituted alkyl;
$R^{17}$ is hydrogen or alkyl or, together with the nitrogen atom to which they are attached, $R^{16}$ and $R^{17}$ form a heterocyclic ring;
Y is $OR^{18}$ or $NR^{19}R^{20}$;
wherein:
$R^{18}$ is hydrogen, alkyl, alkenyl, cycloalkyl, cycloalkenyl, cycloalkyl-substituted alkyl, cycloalkenyl-substituted alkyl, or aryl-substituted alkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, or aryl-substituted alkyl or, together with the nitrogen atom to which they are attached, $R^{19}$ and $R^{20}$ form a heterocyclic ring;

$R^{21}$ is hydrogen or alkyl; and n is 0 to 4;

or a stereoisomer, prodrug, or pharmaceutically acceptable salt, hydrate or N-oxide thereof.

Another embodiment of the invention relates to methods of treating or preventing ileus comprising administering to the patient an effective amount of a peripheral mu opioid antagonist compound.

These and other aspects of the invention will become more apparent from the following detailed description.

DETAILED DESCRIPTION OF THE INVENTION

Figure 1:
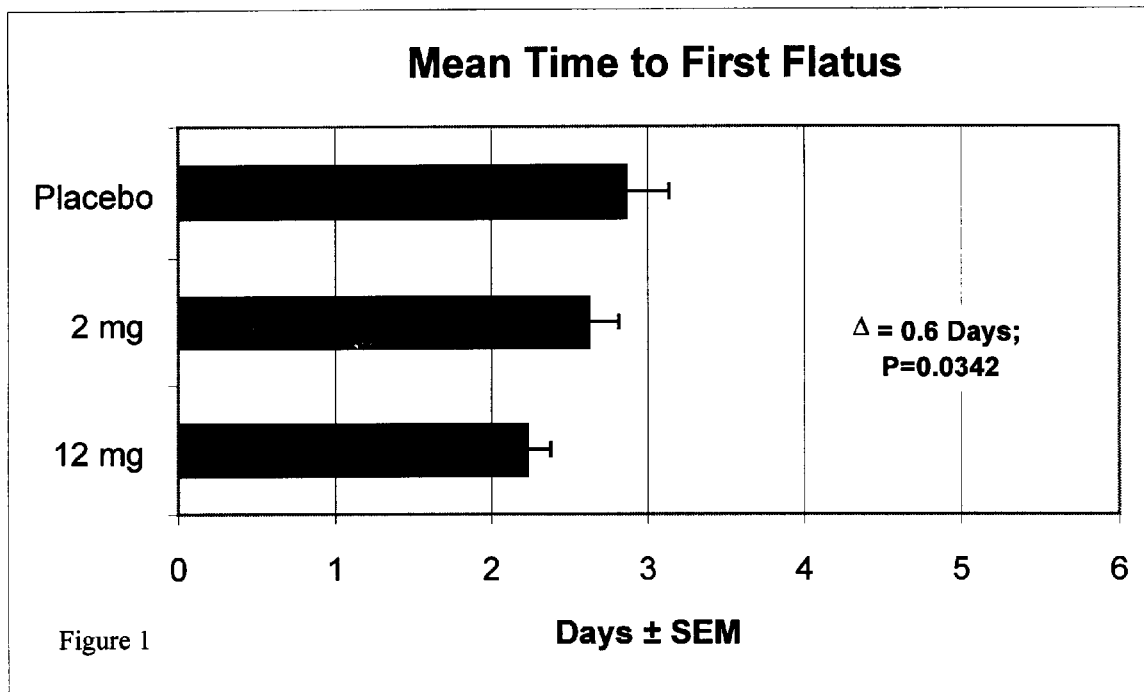
FIGS. 1 to 5 are graphical representations of studies on the treatment of ileus employing methods according to an embodiment of the present invention.

As employed above and throughout the disclosure, the following terms, unless otherwise indicated, shall be understood to have the following meanings.

"Alkyl" refers to an aliphatic hydrocarbon group which may be straight, branched or cyclic having from 1 to about 10 carbon atoms in the chain, and all combinations and subcombinations of ranges therein. "Branched" refers to an alkyl group in which a lower alkyl group, such as methyl, ethyl or propyl, is attached to a linear alkyl chain. In certain preferred embodiments, the alkyl group is a $C_1$–$C_5$ alkyl group, i.e., a branched or linear alkyl group having from 1 to about 5 carbons. In other preferred embodiments, the alkyl group is a $C_1$–$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl and decyl. "Lower alkyl" refers to an alkyl group having 1 to about 6 carbon atoms. Preferred alkyl groups include the lower alkyl groups of 1 to about 3 carbons.

"Alkenyl" refers to an alkyl group containing at least one carbon-carbon double bond and having from 2 to about 10 carbon atoms in the chain, and all combinations and subcombinations of ranges therein. In certain preferred embodiments, the alkenyl group is a $C_2$–$C_{10}$ alkyl group, i.e., a branched or linear alkenyl group having from 2 to about 10 carbons. In other preferred embodiments, the alkenyl group is a $C_2$–$C_6$ alkenyl group, i.e., a branched or linear alkenyl group having from 2 to about 6 carbons. In still other preferred embodiments, the alkenyl group is a $C_3$–$C_{10}$ alkenyl group, i.e., a branched or linear alkenyl group having from about 3 to about 10 carbons. In yet other preferred embodiments, the alkenyl group is a $C_2$–$C_5$ alkenyl group, i.e., a branched or linear alkenyl group having from 2 to about 5 carbons. Exemplary alkenyl groups include, for example, vinyl, propenyl, butenyl, pentenyl hexenyl, heptenyl, octenyl, nonenyl and decenyl groups.

"Alkylene" refers to a straight or branched bivalent aliphatic hydrocarbon group having from 1 to about 6 carbon atoms, and all combinations and subcombinations of ranges therein. The alkylene group may be straight, branched or cyclic. Exemplary alkylene groups include, for example, methylene (—$CH_2$—), ethylene (—$CH_2CH_2$—) and propylene (—$(CH_2)_3$—). There may be optionally inserted along the alkylene group one or more oxygen, sulphur or optionally substituted nitrogen atoms, wherein the nitrogen substituent is alkyl as described previously. Preferred alkylene groups have from about 1 to about 4 carbons.

"Alkenylene" refers to an alkylene group containing at least one carbon-carbon double bond. Exemplary alkenylene groups include, for example, ethenylene (—CH=CH—) and propenylene (—CH=$CHCH_2$—). Preferred alkenylene groups have from 2 to about 4 carbons.

"Cycloalkyl" refers to any stable monocyclic or bicyclic ring having from about 3 to about 10 carbons, and all combinations and subcombinations of ranges therein. In preferred embodiments, the cycloalkyl group is a $C_3$–$C_8$ cycloalkyl group, i.e., a cycloalkyl group having from about 3 to about 8 carbons, with $C_3$–$C_6$ cycloalkyl groups, i.e., cycloalkyl groups having from about 3 to about 6 carbons being more preferred. The cycloalkyl group may be optionally substituted with one or more cycloalkyl group substituents. Preferred cycloalkyl group substituents include alkyl, preferably $C_1$–$C_3$ alkyl, alkoxy, preferably $C_1$–$C_3$ alkoxy, or halo. Exemplary cycloalkyl groups include, for example, cyclopropyl, cyclobutyl, cyclopentyl, cyclohexyl, cycloheptyl and cyclooctyl groups.

"Cycloalkyl-substituted alkyl" refers to a linear alkyl group, preferably a lower alkyl group, substituted at a terminal carbon with a cycloalkyl group, preferably a $C_3$–$C_8$ cycloalkyl group. Typical cycloalkyl-substituted alkyl groups include cyclohexylmethyl, cyclohexylethyl, cyclopentylethyl, cyclopentylpropyl, cyclopropylmethyl and the like.

"Cycloalkenyl" refers to an olefinically unsaturated cycloalkyl group having from about 4 to about 10 carbons, and all combinations and subcombinations of ranges therein. In preferred embodiments, the cycloalkenyl group is a $C_5$–$C_8$ cycloalkenyl group, i.e., a cycloalkenyl group having from about 5 to about 8 carbons.

"Alkoxy" refers to an alkyl-O-group where alkyl is as previously described. Exemplary alkoxy groups include, for example, methoxy, ethoxy, propoxy, butoxy and heptoxy.

"Alkoxy-alkyl" refers to an alkyl-O-alkyl group where alkyl is as previously described.

"Acyl" means an alkyl-CO— group wherein alkyl is as previously described. Preferred acyl groups comprise lower alkyl groups, such as alkyl of about 1 to about 3 carbons. Exemplary acyl groups include acetyl, propanoyl, 2-methylpropanoyl, butanoyl and palmitoyl.

"Aryl" refers to an aromatic carbocyclic radical containing from about 6 to about 10 carbons, and all combinations and subcombinations of ranges therein. The phenyl group may be optionally substituted with one or two or more aryl group substituents. Preferred aryl group substituents include alkyl groups, preferably $C_1$–$C_2$ alkyl groups. Exemplary aryl groups include phenyl and naphthyl.

"Aryl-substituted alkyl" refers to an linear alkyl group, preferably a lower alkyl group, substituted at a terminal carbon with an optionally substituted aryl group, preferably an optionally substituted phenyl ring. Exemplary aryl-substituted alkyl groups include, for example, phenylmethyl, phenylethyl and 3-(4-methylphenyl)propyl.

"Heterocyclic" refers to a monocyclic or multicylic ring system carbocyclic radical containing from about 4 to about 10 members, and all combinations and subcombinations of ranges therein, wherein one or more of the members is an element other than carbon, for example, nitrogen, oxygen or sulfur. The heterocyclic group may be aromatic or nonaromatic. Exemplary heterocyclic groups include, for example, pyrrole and piperidine groups.

"Halo" refers to fluoro, chloro or bromo.

"Effective amount" refers to an amount of a compound as described herein that may be therapeutically effective to prevent or treat the symptoms of particular disorder. Such disorders include, but are not limited to, those pathological disorders associated with ileus, wherein the treatment or prevention comprises, for example, inhibiting the activity thereof by contacting cells, tissues or receptors with compounds of the present invention.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Certain acidic or basic compounds of the present invention may exist as zwitterions. All forms of the compounds, including free acid, free base and zwitterions, are contemplated to be within the scope of the present invention.

"Patient" refers to animals, including mammals, preferably humans.

The present invention is directed to methods for the treatment or prevention of ileus. Different types of ileus may be treated and/or prevented using the methods of the present invention. The present methods are particularly suitable for treating and/or preventing post-surgical ileus and post-partum ileus. "Post-surgical ileus", which may follow surgery such as laparotomy, may be characterized by such symptoms as, for example, obstruction of the gut, particularly in the colon, resulting in nausea, vomiting, lack of passage of flatus and/or stools, abdominal distention and lack of bowel sounds. This condition generally lasts from about 3 to about 5 days, but may endure longer, including up to about one week. Longer durations are generally characteristic of a more severe form of ileus, termed post-surgical paralytic ileus, which may affect other portions of the GI tract in addition to the colon. "Post-partum ileus" generally refers to obstruction of the gut, particularly the colon, following parturition. Both natural and surgically-assisted procedures during parturition may lead to post-partum ileus treated by the present invention. Symptoms of post-partum ileus and post-surgical ileus are similar.

The methods of the present invention may be used to treat patients who are also being administered compounds that may slow gut motility including, for example, opiates and/or opioids, such as opioid analgesics, prior to, during, and subsequent to the onset of ileus. The administration of such opiate or opioid compounds may induce bowel dysfunction which, in turn, may delay recovery from ileus, including postoperative ileus. The methods of the present invention may also be used to treat patients who have not received any exogenous opiates and/or opioids. Thus, in certain embodiments, the present methods comprise administering a compound, discussed in detail below, to patients who have not received any opioid analgesic drugs including, for example, any mu opioid agonists.

While not intending to be bound by any theory or theories of operation, it is contemplated that ileus, particularly post-surgical ileus and post-partum ileus, may result from stress-induced abnormal levels of endogenous opioid compounds. Administration of a mu opioid antagonist according to the methods of the present invention may block interaction of the endogenous opioid compounds with the mu receptors in the gut, thereby preventing and/or inhibiting ileus.

In preferred form, the methods of the present invention involve administering to a patient a compound which is a peripheral mu opioid antagonist compound. The term peripheral designates that the compound acts primarily on physiological systems and components external to the central nervous system, i.e., the compound preferably does not readily cross the blood-brain barrier. In preferred form, the peripheral mu opioid antagonist compounds employed in the methods of the present invention exhibit high levels of activity with respect to gastrointestinal tissue, while exhibiting reduced, and preferably substantially no, central nervous system (CNS) activity. The term "substantially no CNS activity", as used herein, means that less than about 20% of the pharmacological activity of the peripheral mu opioid antagonist compounds employed in the present methods is exhibited in the CNS. In preferred embodiments, the peripheral mu opioid antagonist compounds employed in the present methods exhibit less than about 15% of their pharmacological activity in the CNS, with less than about 10% being more preferred. In even more preferred embodiments, the peripheral mu opioid antagonist compounds employed in the present methods exhibit less than about 5% of their pharmacological activity in the CNS, with about 0% (i.e., no CNS activity) being still more preferred.

In more preferred embodiments, the present methods involve the administration to a patient of a mu peripheral opioid antagonist compound that is a piperidine-N-alkylcarboxylate compound. Preferred piperidine-N-alkylcarboxylate opioid antagonist compounds include, for example, the compounds disclosed in U.S. Pat. Nos. 5,250,542; 5,159,081; 5,270,328; and 5,434,171, the disclosures of which are hereby incorporated herein by reference, in their entireties. A particularly preferred class of piperidine-N-alkylcarboxylate opioid antagonist compounds include those having the following formula (I):

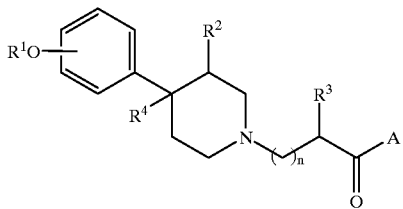

I wherein:
R$^1$ is hydrogen or alkyl;
R$^2$ is hydrogen, alkyl or alkenyl;
R$^3$ is hydrogen, alkyl, alkenyl, aryl, cycloalkyl, cycloalkenyl, cycloalkyl-substituted alkyl, cycloalkenyl-substituted alkyl or aryl-substituted alkyl;
R$^4$ is hydrogen, alkyl or alkenyl;
A is OR$^5$ or NR$^6$R$^7$; wherein:
R$^5$ is hydrogen, alkyl, alkenyl, cycloalkyl, cycloalkenyl, cycloalkyl-substituted alkyl, cycloalkenyl-substituted alkyl, or aryl-substituted alkyl;
R$^6$ is hydrogen or alkyl;
R$^7$ is hydrogen, alkyl, alkenyl, cycloalkyl, aryl, cycloalkyl-substituted alkyl, cycloalkenyl, cycloalkenyl-substituted alkyl, aryl-substituted alkyl, aryl-substituted alkyl, or alkylene substitued B or, together with the nitrogen atom to which they are attached, R$^6$ and R$^7$ form a heterocyclic ring;
B is

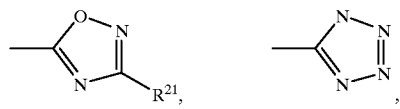

C(=O)W or NR$^8$R$^9$; wherein;
R$^8$ is hydrogen or alkyl;
R$^9$ is hydrogen, alkyl, alkenyl, cycloalkyl-substituted alkyl, cycloalkyl, cycloalkenyl, cycloalkenyl-substituted alkyl, aryl or aryl-substituted alkyl or, together with the nitrogen atom to which they are attached, R$^8$ and R$^9$ form a heterocyclic ring;
W is OR$^{10}$, NR$^{11}$R$^{12}$, or OE; wherein
R$^{10}$ is hydrogen, alkyl, alkenyl, cycloalkyl, cycloalkenyl, cycloalkyl-substituted alkyl, cycloalkenyl-substituted alkyl, or aryl-substituted alkyl;
R$^{11}$ is hydrogen or alkyl;
R$^{12}$ is hydrogen, alkyl, alkenyl, aryl, cycloalkyl, cycloalkenyl, cycloalkyl-substituted alkyl, cycloalkenyl-substituted alkyl, aryl-substituted alkyl or alkylene substituted C(=O)Y or, together with the nitrogen atom to which they are attached, R$^{11}$ and R$^{12}$ form a heterocyclic ring;
E is

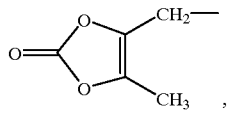

alkylene substituted (C=O)D, or —R$^{13}$OC(=O)R$^{14}$;

wherein
R$^{13}$ is alkyl substituted alkylene;
R$^{14}$ is alkyl;
D is OR$^{15}$ or NR$^{16}$R$^{17}$;
wherein:
R$^{15}$ is hydrogen, alkyl, alkenyl, cycloalkyl, cycloalkenyl, cycloalkyl-substituted alkyl, cycloalkenyl-substituted alkyl, or aryl-substituted alkyl;
R$^{16}$ is hydrogen, alkyl, alkenyl, aryl, aryl-substituted alkyl, cycloalkyl, cycloalkenyl, cycloalkyl-substituted alkyl or cycloalkenyl-substituted alkyl;
R$^{17}$ is hydrogen or alkyl or, together with the nitrogen atom to which they are attached, R$^{16}$ and R$^{17}$ form a heterocyclic ring;
Y is OR$^{18}$ or NR$^{19}$R$^{20}$;
wherein:
R$^{18}$ is hydrogen, alkyl, alkenyl, cycloalkyl, cycloalkenyl, cycloalkyl-substituted alkyl, cycloalkenyl-substituted alkyl, or aryl-substituted alkyl;
R$^{19}$ is hydrogen or alkyl;
R$^{20}$ is hydrogen, alkyl, alkenyl, aryl, cycloalkyl, cycloalkenyl, cycloalkyl-substituted alkyl, cycloalkenyl-substituted alkyl, or aryl-substituted alkyl or, together with the nitrogen atom to which they are attached, R$^{19}$ and R$^{20}$ form a heterocyclic ring;
R$^{21}$ is hydrogen or alkyl; and
n is 0 to about 4;
or a stereoisomer, prodrug, or pharmaceutically acceptable salt, hydrate or N-oxide thereof.

In the above formula (I), R$^1$ is hydrogen or alkyl. In preferred embodiments, R$^1$ is hydrogen or C$_1$–C$_5$alkyl. In even more preferred embodiments, R$^1$ is hydrogen.

In the above formula (I), R$^2$ is hydrogen, alkyl or alkenyl. In preferred embodiments, R$^2$ is hydrogen, C$_1$–C$_5$alkyl or C$_2$–C$_6$alkenyl. Also in preferred embodiments, R$^2$ is alkyl, with C$_1$–C$_3$alkyl being more preferred.

In the above formula (I), R$^3$ is hydrogen, alkyl, alkenyl, aryl, cycloalkyl, cycloalkenyl, cycloalkyl-substituted alkyl, cycloalkenyl-substituted alkyl or aryl-substituted alkyl. In preferred embodiments, R$^3$ is hydrogen, C$_1$–C$_{10}$alkyl, C$_3$–C$_{10}$alkenyl, phenyl, cycloalkyl, C$_5$–C$_8$cycloalkenyl, cycloalkyl-substituted C$_1$–C$_3$alkyl, C$_5$–C$_8$cycloalkyl-substituted C$_1$–C$_3$alkyl or phenyl-substituted C$_1$–C$_3$ alkyl. In more preferred embodiments, R$^3$ is benzyl, phenyl, cyclohexyl, or cyclohexylmethyl.

In the above formula (I), R$^4$ is hydrogen, alkyl or alkenyl. In preferred embodiments, R$^4$ is hydrogen, C$_1$–C$_5$alkyl or C$_2$–C$_6$alkenyl. In more preferred embodiments, R$^4$ is C$_1$–C$_3$alkyl, with methyl being even more preferred.

In the above formula (I), A is OR$^5$ or NR$^6$R$^7$.

In the above formula (I), R$^5$ is hydrogen, alkyl, alkenyl, cycloalkyl, cycloalkenyl, cycloalkyl-substituted alkyl, cycloalkenyl-substituted alkyl, or aryl-substituted alkyl. In preferred embodiments, R$^5$ is hydrogen, C$_1$–C$_{10}$alkyl, C$_2$–C$_{10}$alkenyl, cycloalkyl, C$_5$–C$_8$cycloalkenyl, cycloalkyl-substituted C$_1$–C$_3$ alkyl, C$_5$–C$_8$cycloalkenyl-substituted C$_1$–C$_3$alkyl, or phenyl-substituted C$_1$–C$_3$alkyl. Also in preferred embodiments, R$^5$ is hydrogen or alkyl, with C$_1$–C$_3$alkyl being more preferred.

In the above formula (I), R$^6$ is hydrogen or alkyl. Preferably, R$^6$ is hydrogen or C$_1$–C$_3$alkyl. Even more preferably, R$^6$ is hydrogen.

In the above formula (I), R$^7$ is hydrogen, alkyl, alkenyl, cycloalkyl, aryl, cycloalkyl-substituted alkyl, cycloalkenyl, cycloalkenyl-substituted alkyl, aryl-substituted alkyl, aryl-substituted alkyl or alkylene substituted B. In preferred embodiments, $R^7$ is hydrogen, $C_1$–$C_{10}$alkyl, $C_3$–$C_{10}$alkenyl, phenyl, cycloalkyl, cycloalkyl-substituted $C_1$–$C_3$alkyl, $C_5$–$C_8$cycloalkenyl, $C_5$–$C_8$cycloalkenyl-substituted $C_1$–$C_3$alkyl, phenyl-substituted $C_1$–$C_3$alkyl or $(CH_2)_q$—B. In more preferred embodiments, $R^7$ is $(CH_2)_q$—B.

In certain alternative embodiments, in the above formula (I), $R^6$ and $R^7$ form, together with the nitrogen atom to which they are attached, a heterocyclic ring.

The group B in the definition of $R^7$ is

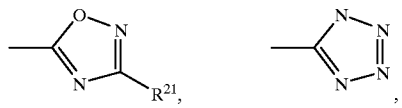

$C(=O)W$ or $NR^8R^9$. In preferred embodiments, B is $C(=O)W$.

The group $R^8$ in the definition of B is hydrogen or alkyl. In preferred embodiments, $R^8$ is hydrogen or $C_1$–$C_3$alkyl.

The group $R^9$ in the definition of B is hydrogen, alkyl, alkenyl, cycloalkyl-substituted alkyl, cycloalkyl, cycloalkenyl, cycloalkenyl-substituted alkyl, aryl or aryl-substituted alkyl. In preferred embodiments, $R^9$ is hydrogen, $C_1$–$C_{10}$alkyl, $C_3$–$C_{10}$alkenyl, cycloalkyl-substituted $C_1$–$C_3$alkyl, cycloalkyl, $C_5$–$C_8$cycloalkenyl, $C_5$–$C_8$cycloalkenyl-substituted $C_1$–$C_3$alkyl, phenyl or phenyl-substituted $C_1$–$C_3$alkyl.

In certain alternative embodiments, in the definition of B, $R^8$ and $R^9$ form, together with the nitrogen atom to which they are attached, a heterocyclic ring.

The group W in the definition of B is $OR^{10}$, $NR^{11}R^{12}$ or OE.

The group $R^{10}$ in the definition of W is hydrogen, alkyl, alkenyl, cycloalkyl, cycloalkenyl, cycloalkyl-substituted alkyl, cycloalkenyl-substituted alkyl, or aryl-substituted alkyl. In preferred embodiments, $R^{10}$ is hydrogen, $C_1$–$C_{10}$alkyl, $C_2$–$C_{10}$alkenyl, cycloalkyl, $C_5$–$C_8$cycloalkenyl, cycloalkyl-substituted $C_1$–$C_3$alkyl, $C_5$–$C_8$cycloalkenyl-substituted $C_1$–$C_3$alkyl, or phenyl-substituted $C_1$–$C_3$alkyl. Also in preferred embodiments, $R^{10}$ is hydrogen, alkyl, preferably $C_1$–$C_5$alkyl, phenyl-substituted alkyl, preferably phenyl-substituted $C_1$–$C_2$alkyl, cycloalkyl or cycloalkyl-substituted alkyl, preferably $C_5$–$C_6$cycloalkyl-substituted $C_1$–$C_3$alkyl.

The group $R^{11}$ in the definition of W is hydrogen or alkyl. In preferred embodiments, $R^{11}$ is hydrogen or $C_1$–$C_3$alkyl.

The group $R^{12}$ in the definition of W is hydrogen, alkyl, alkenyl, aryl, cycloalkyl, cycloalkenyl, cycloalkyl-substituted alkyl, cycloalkenyl-substituted alkyl, aryl-substituted alkyl or alkylene-substituted $C(=O)Y$. In preferred embodiments, $R^{12}$ is hydrogen, $C_1$–$C_{10}$alkyl, $C_3$–$C_{10}$alkenyl, phenyl, cycloalkyl, $C_5$–$C_8$cycloalkenyl, cycloalkyl-substituted $C_1$–$C_3$alkyl, $C_5$–$C_8$cycloalkenyl-substituted $C_1$–$C_3$alkyl, phenyl-substituted $C_1$–$C_3$alkyl, or alkylene-substituted $C(=O)Y$. Also in preferred embodiments, $R^{12}$ is hydrogen, alkyl, preferably $C_1$–$C_3$alkyl or $(CH_2)_mC(O)Y$, where m is 1 to 4.

The group Y in the definition of $R^{12}$ is $OR^{18}$ or $NR^{19}R^{20}$.

In certain alternative embodiments, in the definition of W, $R^{12}$ and $R^{13}$ form, together with the nitrogen atom to which they are attached, a heterocyclic ring.

The group E in the definition of W is

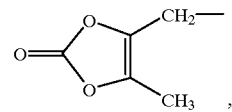

alkylene substituted $(C=O)D$, or —$R^3OC(=O)R^4$. In preferred embodiments, E is

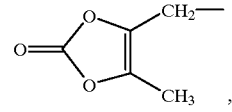

$(CH_2)_m(C=O)D$ (where m is as defined above), or —$R^{13}OC(=O)R^{14}$.

The group $R^{13}$ in the definition of E is alkyl substituted alkylene. In preferred embodiments, $R^{13}$ is $C_1$–$C_3$alkyl substituted methylene. In more preferred embodiments, $R^{13}$ is —$CH(CH_3)$— or —$CH(CH_2CH_3)$—.

The group $R^{14}$ in the definition of E is alkyl. In preferred embodiments, $R^{14}$ is $C_1$–$C_{10}$alkyl.

The group D in the definition of E is D is $OR^{15}$ or $NR^{16}R^{17}$.

The group $R^{15}$ in the definition of D is hydrogen, alkyl, alkenyl, cycloalkyl, cycloalkenyl, cycloalkyl-substituted alkyl, cycloalkenyl-substituted alkyl, or aryl-substituted alkyl. In preferred embodiments, $R^{15}$ is hydrogen, $C_1$–$C_{10}$alkyl, $C_2$–$C_{10}$alkenyl, cycloalkyl, $C_5$–$C_8$cycloalkenyl, cycloalkyl-substituted $C_1$–$C_3$alkyl, $C_5$–$C_8$cycloalkenyl-substituted $C_1$–$C_3$alkyl, or phenyl-substituted $C_1$–$C_3$alkyl. Also in preferred embodiments, $R^{15}$ is hydrogen or alkyl, with $C_1$–$C_3$alkyl being more preferred.

The group $R^{16}$ in the definition of D is hydrogen, alkyl, alkenyl, aryl, aryl-substituted alkyl, cycloalkyl, cycloalkenyl, cycloalkyl-substituted alkyl or cycloalkenyl-substituted alkyl. In preferred embodiments, $R^{16}$ is hydrogen, $C_1$–$C_{10}$alkyl, $C_3$–$C_{10}$alkenyl, phenyl, phenyl-substituted $C_1$–$C_3$alkyl, cycloalkyl, $C_5$–$C_8$cycloalkenyl, cycloalkyl-substituted $C_1$–$C_3$alkyl, $C_5$–$C_8$cycloalkenyl-substituted $C_1$–$C_3$alkyl. In even more preferred embodiments, $R^{16}$ is methyl or benzyl.

The group $R^{17}$ in the definition of D is hydrogen or alkyl. In preferred embodiments, $R^{17}$ is hydrogen or $C_1$–$C_3$ alkyl. In even more preferred embodiments, $R^{17}$ is hydrogen.

In certain alternative embodiments, in the definition of D, $R^{16}$ and $R^{17}$ form, together with the nitrogen atom to which they are attached, a heterocyclic ring.

The group $R^{18}$ in the definition of Y is hydrogen, alkyl, alkenyl, cycloalkyl, cycloalkenyl, cycloalkyl-substituted alkyl, cycloalkenyl-substituted alkyl, or aryl-substituted alkyl. In preferred embodiments, $R^{18}$ is hydrogen, $C_1$–$C_{10}$alkyl, $C_2$–$C_{10}$alkenyl, cycloalkyl, $C_5$–$C_8$cycloalkenyl, cycloalkyl-substituted $C_1$–$C_3$ alkyl, $C_5$–$C_8$cycloalkenyl-substituted $C_1$–$C_3$alkyl, or phenyl-substituted $C_1$–$C_3$alkyl. In more preferred embodiments, $R^{18}$ is hydrogen or $C_1$–$C_3$alkyl.

The group $R^{19}$ in the definition of Y is hydrogen or alky. In preferred embodiments, $R^{19}$ is hydrogen or $C_1$–$C_3$alkyl.

The group $R^{20}$ in the definition of Y is hydrogen, alkyl, alkenyl, aryl, cycloalkyl, cycloalkenyl, cycloalkyl-substituted alkyl, cycloalkenyl-substituted alkyl, or aryl-substituted alkyl. In preferred embodiments, $R^{20}$ is hydrogen, $C_1$–$C_{10}$alkyl, $C_3$–$C_{10}$alkenyl, phenyl, cycloalkyl, $C_5$–$C_8$cycloalkenyl, cycloalkyl-substituted $C_1$–$C_3$alkyl, $C_5$–$C_8$cycloalkenyl-substituted $C_1$–$C_3$alkyl, or phenyl-substituted $C_1$–$C_3$alkyl. In more preferred embodiments, $R^{20}$ is hydrogen or $C_1$–$C_3$alkyl.

In certain alternative embodiments, in the definition of Y, $R^{19}$ and $R^{20}$ form, together with the nitrogen atom to which they are attached, a heterocyclic ring.

The group $R^{21}$ in the definition of B is hydrogen or alkyl. Preferably, $R^{21}$ is hydrogen or $C_1$–$C_3$alkyl. Even more preferably, $R^{21}$ is hydrogen.

In the above formula (I), n is 0 to about 4. In preferred embodiments, n is about 1 or 2.

In the above definition of $R^7$, q is about 1 to about 4. In preferred embodiments, q is about 1 to about 3.

In the above definition of E, m is about 1 to about 4. In preferred embodiments, m is about 1 to about 3.

The compounds of formula (I) can occur as the trans and cis stereochemical isomers by virtue of the substituents at the 3- and 4-positions of the piperidine ring, and such stereochemical isomers are within the scope of the claims. The term "trans", as used herein, refers to $R^2$ in position 3 being on the opposite side from the methyl group in position 4, whereas in the "cis" isomer $R^2$ and the 4-methyl are on the same side of the ring. In the methods of the present invention, the compounds employed may be the individual stereoisomers, as well as mixtures of stereoisomers. In the most preferred embodiments, the methods of the present invention involve compounds of formula (I) wherein the group $R^2$ at the 3-position is situated on the opposite side of the ring, i.e., trans to the methyl group in the 4-position and on the same side of the ring. These trans isomers can exist as the 3R,4R-isomer, or the 3S,4S-isomer.

The terms "R" and "S" are used herein as commonly used in organic chemistry to denote specific configuration of a chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counterclockwise relationship of group priorities (highest to second lowest) when viewed along the bond toward the lowest priority group. The priority of groups is based upon their atomic number (heaviest isotope first). A partial list of priorities and a discussion of stereochemistry is contained in the book: *The Vocabulary of Organic Chemistry,* Orchin, et al., John Wiley and Sons Inc., page 126 (1980), which is incorporated herein by reference in its entirety.

Preferred piperidine-N-alkylcarboxylate compounds for use in the methods of the present invention are those of formula (I) in which the configuration of substituents on the piperidine ring is 3R and 4R.

When $R^3$ is not hydrogen, the carbon atom to which $R^3$ is attached is asymmetric. As such, this class of compounds can further exist as the individual R or S stereoisomers at this chiral center, or as mixtures of stereoisomers, and all are contemplated within the scope of the present invention. Preferably, a substantially pure stereoisomer of the compounds of this invention is used, i.e., an isomer in which the configuration at the chiral center to which $R^3$ is attached is R or S, i.e., those compounds in which the configuration at the three chiral centers is preferably 3R, 4R, S or 3R, 4R, R.

Furthermore, other asymmetric carbons can be introduced into the molecule depending on the structure of A. As such, these classes of compounds can exist as the individual R or S stereoisomers at these chiral centers, or as mixtures of stereoisomers, and all are contemplated as being within the scope of methods of the present invention.

Preferred piperidine-N-alkylcarboxylate compounds for use in the methods of the present invention include the following:
U—OCH$_2$CH$_3$; U—OH; G—OH; U—NHCH$_2$C(O)NHCH$_3$; U—NHCH$_2$C(O)NH$_2$; G—NHCH$_2$C(O)NHCH$_3$; U—NHCH$_2$C(O)NHCH$_2$CH$_3$; G—NH(CH$_2$)$_3$C(O)OCH$_2$CH$_3$; G—NHCH$_2$C(O)OH; M—NHCH$_2$C(O)NH$_2$; M—NH(CH$_2$)$_2$C(O)OCH$_2$(C$_6$H$_5$); X—OCH$_2$CH$_3$; X—OH; X—NH(CH$_2$)$_2$CH$_3$; Z—NH(CH$_2$)$_3$C(O)OCH$_2$CH$_3$; X—NHCH$_2$C(O)OH; Z—NH(CH$_2$)$_2$N(CH$_3$)$_2$; Z—NH(CH$_2$)$_2$C(O)NHCH$_2$CH$_3$; X—OCH$_2$(C$_6$H$_5$); X—N(CH$_3$)$_2$; Z—NH(CH$_2$)$_3$C(O)NHCH$_3$; Z—NH(CH$_2$)$_3$C(O)NH$_2$; Z—NH(CH$_2$)$_3$C(O)NHCH$_2$CH$_3$; X—OCH$_2$C(O)OCH$_3$; X—OCH$_2$C(O)NHCH$_3$; and X—N(CH$_3$)CH$_2$C(O)CH$_2$CH$_3$; in which:

U represents

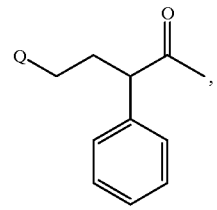

G represents

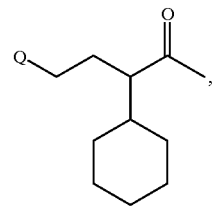

M represents

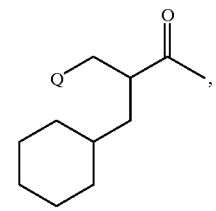

Z represents

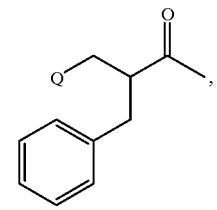

X represents —ZNHCH$_2$C(=O)—;
wherein Q represents

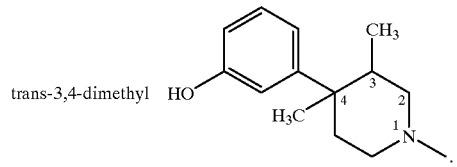

trans-3,4-dimethyl

Particularly preferred piperidine-N-alkylcarboxylate compounds for use in the methods of the present invention include the following:

Z—OH; Z—NH(CH$_2$)$_2$C(O)OH; G—NH(CH$_2$)$_2$C(O)NH$_2$; G—NH(CH$_2$)$_2$C(O)NHCH$_3$; G—NHCH$_2$C(O)NH$_2$; G—NHCH$_2$C(O)NHCH$_2$CH$_3$; G—NH(CH$_2$)$_3$C(O)NHCH$_3$; G—NH(CH$_2$)$_2$C(O)OH; G—NH(CH$_2$)$_3$C(O)OH; X—NH$_2$; X—NHCH(CH$_3$)$_2$; X—OCH$_2$CH(CH$_3$)$_2$; X—OCH$_2$C$_6$H$_5$; X—OH; X—O(CH$_2$)$_4$CH$_3$; X—O—(4-methoxycyclohexyl); X—OCH(CH$_3$)OC(O)CH$_3$; X—OCH$_2$C(O)NHCH$_2$(C$_6$H$_5$); M—NHCH$_2$C(O)OH; M—NH(CH$_2$)$_2$C(O)OH; M—NH(CH$_2$)$_2$C(O)NH$_2$; U—NHCH$_2$C(O)OCH$_2$CH$_3$; and U—NHCH$_2$C(O)OH; wherein Z, G, X, M and U are as defined above.

Stated another way, in accordance with preferred embodiments of the invention, the compound of formula (I) has the formula Q—CH$_2$CH(CH$_2$(C$_6$H$_5$))C(O)OH, Q—CH$_2$CH$_2$CH(C$_6$H$_5$)C(O)NHCH$_2$C(O)OCH$_2$CH$_3$, Q—CH$_2$CH$_2$CH(C$_6$H$_5$)C(O)NHCH$_2$C(O)OH, Q—CH$_2$CH$_2$CH(C$_6$H$_5$)C(O)NHCH$_2$C(O)NHCH$_3$, Q—CH$_2$CH$_2$CH(C$_6$H$_5$)C(O)NHCH$_2$C(O)NHCH$_2$CH$_3$, G—NH(CH$_2$)$_2$C(O)NH$_2$, G—NH(CH$_2$)$_2$C(O)NHCH$_3$, G—NHCH$_2$C(O)NH$_2$, G—NHCH$_2$C(O)NHCH$_3$, G—NHCH$_3$C(O)NHCH$_2$CH$_3$, G—NH(CH$_2$)$_3$C(O)OCH$_2$CH$_3$, G—NH(CH$_2$)$_3$C(O)NHCH$_3$, G—NH(CH$_2$)$_2$C(O)OH, G—NH(CH$_2$)$_3$C(O)OH, Q—CH$_2$CH(CH$_2$(C$_6$H$_{11}$))C(O)NHCH$_2$C(O)OH, Q—CH$_2$CH(CH$_2$(C$_6$H$_{11}$))C(O)NH(CH$_2$)$_2$C(O)OH, Q—CH$_2$CH(CH$_2$(C$_6$H$_{11}$))C(O)NH(CH$_2$)$_2$C(O)NH$_2$, Z—NHCH$_2$C(O)OCH$_2$CH$_3$, Z—NHCH$_2$C(O)OH, Z—NHCH$_2$C(O)NH$_2$, Z—NHCH$_2$C(O)N(CH$_3$)$_2$, Z—NHCH$_2$C(O)NHCH(CH$_3$)$_2$, Z—NHCH$_2$C(O)OCH$_2$CH(CH$_3$)$_2$, Z—NH(CH$_2$)$_2$C(O)OCH$_2$(C$_6$H$_5$), Z—NH(CH$_2$C(O)OH, Z—NH(CH$_2$)$_2$C(O)NHCH$_2$CH$_3$, Z—NH(CH$_2$)$_3$C(O)NHCH$_3$, Z—NHCH$_2$C(O)NHCH$_2$C(O)OH, Z—NHCH$_2$C(O)OCH$_2$C(O)OCH$_3$, Z—NHCH$_2$C(O)O(CH$_2$)$_4$CH$_3$, Z—NHCH$_2$C(O)OCH$_2$C(O)NHCH$_3$, Z—NHCH$_2$C(O)O—(4-methoxycyclohexyl), Z—NHCH$_2$C(O)OCH$_2$C(O)NHCH$_2$(C$_6$H$_5$) or Z—NHCH$_2$C(O)OCH(CH$_3$)OC(O)CH$_3$;
wherein Q, G and Z are as defined above.

In even more preferred embodiments, the compound of formula (I) has the formula (3R,4R,S)-Z—NHCH$_2$C(O)OCH$_2$CH(CH$_3$)$_2$, (+)-Z—NHCH$_2$C(O)OH, (-)-Z—NHCH$_2$C(O)OH, (3R,4R,R)-Z—NHCH$_2$C(O)—OCH$_2$CH(CH$_3$)$_2$, (3S,4S,S)-Z—NHCH$_2$C(O)OCH$_2$CH(CH$_3$)$_2$, (3S,4S,R)-Z—NHCH$_2$C(O)OCH$_2$CH(CH$_3$)$_2$, (3R,4R)-Z—NHCH$_2$C(O)NHCH$_2$(C$_6$ H$_5$) or (3R,4R)-G—NH(CH$_2$)$_3$C(O)OH, where Z and G are as defined above. In still more preferred embodiments, the compound of formula (I) has the formula (+)-Z—NHCH$_2$C(O)OH or (-)-Z—NHCH$_2$C(O)OH where Z is as defined above.

Compounds of formula (I) that act locally on the gut, have high potency, and are orally active are most preferred. A particularly preferred embodiment of the present invention is the compound (+)-Z—NHCH$_2$C(O)OH, i.e., the compound of the following formula (II).

II

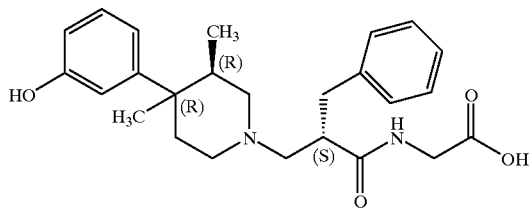

The compound of formula (II) has low solubility in water except at low or high pH conditions. Zwitterionic character may be inherent to the compound, and may impart desirable properties such as poor systemic absorption and sustained local affect on the gut following oral administration.

In an alternate embodiment, the methods of the present invention may involve administering to a patient a peripheral mu opioid antagonist compound that is a quaternary morphinan compound. Examples of quaternary morphinan compounds that may be suitable for use in the methods of the present invention include, for example, quaternary salts of N-methylnaltrexone, N-methylnaloxone, N-methylnalorphine, N-diallylnormorphine, N-allyllevallorphan and N-methylnalmefene.

In yet another alternate embodiment, the methods of the present invention may involve administering to a patient a peripheral mu opioid antagonist compound in the form of an opium alkaloid derivative. The term "opium alkaloid derivative", as used herein, refers to peripheral mu opioid antagonist compounds that are synthetic or semi-synthetic derivatives or analogs of opium alkaloids. In preferred form, the opium alkaloid derivatives employed in the methods of the present invention exhibit high levels of morphine antagonism, while exhibiting reduced, and preferably substantially no, agonist activity. The term "substantially no agonist activity", as used herein in connection with the opium alkaloid derivatives, means that the maximal response with respect to electrically stimulated guinea pig ileum, at a concentration of 1 $\mu$M, is about 60% or less relative to morphine. In preferred embodiments, the opium alkaloid derivatives employed in the present methods have a maximal response with respect to guinea pig ileum, at a concentration of 1 $\mu$M, of about 50% or less relative to morphine, with a maximal response of about 40% or less being more preferred. In even more preferred embodiments, the opium alkaloid derivatives employed in the present methods have a maximal response with respect to guinea pig ileum, at a concentration of 1 $\mu$M, of about 30% or less relative to morphine, with a maximal response of about 20% or less being more preferred. In still more preferred embodiments, the opium alkaloid derivatives employed in the present methods have a maximal response with respect to guinea pig ileum, at a concentration of 1 $\mu$M, of about 10% or less relative to morphine. In certain particularly preferred embodiments, the opium alkaloid derivatives have a maximal response with respect to guinea pig ileum, at a concentration of 1 $\mu$M, of about 0% (i.e., no response).

Suitable methods for determining maximal response of opium alkaloid derivatives with respect to electrically stimulated guinea pig ileum are described, for example, in U.S. Pat. Nos. 4,730,048 and 4,806,556, the disclosures of which are hereby incorporated herein by reference, in their entireties.

In preferred form, the opium alkaloid derivatives employed in the methods of the present invention have the following formulas (III) or (IV):

III

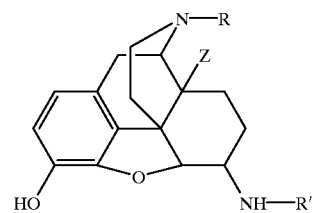

or

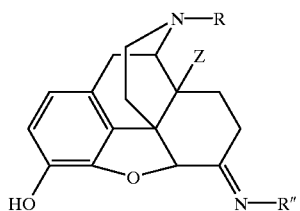

wherein:
R is alkyl, cycloalkyl-substituted alkyl, aryl, aryl-substituted alkyl or alkenyl;
Z is hydrogen or OH;
R' is X'-J(L)(T), wherein:
J is alkylene or alkenylene;
L is hydrogen, amino, or alkyl optionally substituted with $CO_2H$, OH or phenyl; and
T is $CO_2H$, $SO_3H$, amino or guanidino;
X' is a direct bond or C(=O); and
R" is NH-J(L)(T) or guanidino;
or a stereoisomer, prodrug, or pharmaceutically acceptable salt, hydrate or N-oxide thereof.

In the compounds of formulas (III) and (IV) above, R is alkyl, cycloalkyl-substituted alkyl, aryl, aryl-substituted alkyl or alkenyl. In preferred embodiments, R is $C_1$–$C_5$alkyl, $C_3$–$C_6$cycloakyl-substituted alkyl, aryl, arylalkyl or trans-$C_2$–$C_5$alkenyl. In more preferred embodiments, R is $C_1$–$C_3$alkyl, allyl or cyclopropylmethyl, with cyclopropylmethyl being even more preferred.

In the compounds of formulas (III) and (I) above, Z is hydrogen or OH. In preferred embodiments, Z is OH.

In the compounds of formulas (III) and (IV), R' is X-J(L)(T) and R" is NH-J(L)(T) or guanidino.

In the definitions of R' and R", G is alkylene or alkenylene. In preferred embodiments, J is $C_1$–$C_5$alkylene, $C_2$–$C_6$alkylene interrupted by an oxygen atom, or $C_2$–$C_5$alkenylene.

In the definitions of R' and R", L is hydrogen, amino, or alkyl optionally substituted with $CO_2H$, OH or phenyl. In preferred embodiments, L is hydrogen, amino, or $C_1$–$C_5$alkyl optionally substituted with $CO_2H$, OH or phenyl. In more preferred embodiments, L is hydrogen or amino.

In the definitions of R' and R", T is $CO_2H$, $SO_3H$, amino or guanidino. In preferred embodiments, T is $CO_2H$ or guanidino.

In the definition of R', X is a direct bond or C(=O).

Preferred opioid alkaloid derivatives that may be employed in the methods of the present invention include compounds of formula (III) wherein R is cyclopropylmethyl, Z is OH, and R' is selected from C(=O)$(CH_2)_2CO_2H$, C(=O)$(CH_2)_3CO_2H$, C(=O)CH=CHCO$_2$H, C(=O)CH$_2$OCH$_2$CO$_2$H, C(=O)CH(NH$_2$)(CH$_2$)$_3$NHC(=NH)NH$_2$ or C(=O)CH(NH$_2$)CH$_2$CO$_2$H. Also preferred are opioid alkaloid derivatives of formula (III) wherein R is cyclopropylmethyl, Z is OH, and R' is CH$_2$CO$_2$H. In other preferred embodiments, the opioid alkaloid derivatives that may be employed in the methods of the present invention include compounds of formula (IV) wherein R is cyclopropylmethyl, Z is OH, and R" is NHCH$_2$CO$_2$H.

Other opioid alkaloid derivatives that may be employed in the methods of the present invention are described, for example, in U.S. Pat. Nos. 4,730,048 and 4,806,556, the disclosures of which are hereby incorporated herein by reference, in their entireties.

In still another alternate embodiment, the methods of the present invention may involve administering to a patient a peripheral mu opioid antagonist compound in the form of a quaternary benzomorphan compound. In preferred form, the quaternary benzomorphan compounds employed in the methods of the present invention exhibit high levels of morphine antagonism, while exhibiting reduced, and preferably substantially no, agonist activity. The term "substantially no agonist activity", as used herein in connection with the quaternary benzomorphan compounds, means that the maximal response with respect to electrically stimulated guinea pig ileum, at a concentration of 1 μM, is about 60% or less relative to morphine. In preferred embodiments, the quaternary benzomorphan compounds employed in the present methods have a maximal response with respect to guinea pig ileum, at a concentration of 1 μM, of about 50% or less relative to morphine, with a maximal response of about 40% or less being more preferred. In even more preferred embodiments, the quaternary benzomorphan compounds employed in the present methods have a maximal response with respect to guinea pig ileum, at a concentration of 1 μM, of about 30% or less relative to morphine, with a maximal response of about 20% or less being more preferred. In still more preferred embodiments, the quaternary benzomorphan compounds employed in the present methods have a maximal response with respect to guinea pig ileum, at a concentration of 1 μM, of about 10% or less relative to morphine. In certain particularly preferred embodiments, the quaternary benzomorphan compounds have a maximal response with respect to guinea pig ileum, at a concentration of 1 μM, of about 0% (i.e., no response).

In preferred form, the quaternary benzomorphan compounds employed in the methods of the present invention have the following formula (V):

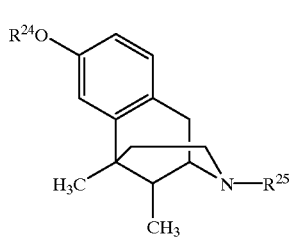

where:
$R^{24}$ is hydrogen or acyl; and
$R^{25}$ is alkyl or alkenyl;
or a stereoisomer, prodrug, or pharmaceutically acceptable salt, hydrate or N-oxide thereof.

In the above formula (V), $R^{24}$ is hydrogen or acyl. In preferred embodiments, $R^{24}$ is hydrogen or $C_1$–$C_6$ acyl. In more preferred embodiments, $R^{24}$ is hydrogen or $C_1$–$C_2$ acyl. In even more preferred embodiments, $R^{24}$ is hydrogen or acetoxy, with hydrogen being still more preferred.

In the above formula (V), $R^{25}$ is alkyl or alkenyl. In preferred embodiments, $R^{25}$ is $C_1$–$C_6$ alkyl or $C_2$–$C_6$ alkenyl. In even more preferred embodiments, $R^{25}$ is $C_1$–$C_3$ alkyl or $C_2$–$C_3$ alkenyl. In still more preferred embodiments, $R^{25}$ is propyl or allyl.

Preferred quaternary benzomorphan compounds that may be employed in the methods of the present invention include the following compounds of formula (V): 2'-hydroxy-5,9-dimethyl-2,2-diallyl-6,7-benzomorphanium-bromide;

2'-hydroxy-5,9-dimethyl-2-n-propyl-6,7-benzomorphan; 2'-hydroxy-5,9-dimethyl-2-allyl-6,7-benzomorphan; 2'-hydroxy-5,9-dimethyl-2-n-propyl-2-allyl-6,7-benzomorphanium-bromide; 2'-hydroxy-5,9-dimethyl-2-n-propyl-2-propargyl-6,7-benzomorphanium-bromide; and 2'-acetoxy-5,9-dimethyl-2-n-propyl-2-allyl-6,7-benzomorphanium-bromide.

Other quaternary benzomorphan compounds that may be employed in the methods of the present invention are described, for example, in U.S. Pat. No. 3,723,440, the disclosures of which are hereby incorporated herein by reference, in their entirety.

Other mu opioid antagonist compounds which may be employed in the methods of the present invention, in addition to those exemplified above, would be readily apparent to one of ordinary skill in the art, once armed with the teachings of the present disclosure.

The compounds employed in the methods of the present invention may exist in prodrug form. As used herein, "prodrug" is intended to include any covalently bonded carriers which release the active parent drug according to formulas (I) to (IV) or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley& Sons, 1991.

Piperidine-N-alkylcarboxylate compounds according to the present invention may be synthesized employing methods taught, for example, in U.S. Pat. Nos. 5,250,542, 5,434, 171, 5,159,081, and 5,270,328, the disclosures of which are hereby incorporated herein by reference in their entireties. For example, the 3-substituted-4-methyl-4-(3-hydroxy- or alkanoyloxyphenyl)piperidine derivatives employed as starting materials in the synthesis of the present compounds may be prepared by the general procedure taught in U.S. Pat. No. 4,115,400 and U.S. Pat. No. 4,891,379, the disclosures of which are hereby incorporated herein by reference in their entireties. The starting material for the synthesis of compounds described herein, (3R,4R)-4-(3-hydroxypheny)-3,4-dimethylpiperidine, may be prepared by the procedures described in U.S. Pat. No. 4,581,456, the disclosures of which are hereby incorporated herein by reference, in their entirety, but adjusted as described such that the β-stereochemistry is preferred.

The first step of the process may involves the formation of the 3-alkoxyphenyllithium reagent by reacting 3-alkoxybromobenzene with an alkyllithium reagent. This reaction may be performed under inert conditions and in the presence of a suitable non-reactive solvent such as dry diethyl ether or preferably dry tetrahydrofuran. Preferred alkyllithium reagents used in this process are n-butyllithium, and especially sec-butyllithium. Generally, approximately an equimolar to slight excess of alkyllithium reagent may be added to the reaction mixture. The reaction may be conducted at a temperature of from about −20° C. and about −100° C., more preferably from about −50° C. to about −55° C.

Once the 3-alkoxyphenyllithium reagent has formed, approximately an equimolar quantity of a 1-alkyl-4-piperidone may be added to the mixture while maintaining the temperature between −20° C. and −100° C. The reaction is typically complete after about 1 to 24 hours. At this point, the reaction mixture may be allowed to gradually warm to room temperature. The product may be isolated by the addition to the reaction mixture of a saturated sodium chloride solution to quench any residual lithium reagent. The organic layer may be separated and further purified if desired to provide the appropriate 1-alkyl-4-(3-alkoxyphenyl) piperidinol derivative.

The dehydration of the 4-phenylpiperidinol prepared above may be accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid in toluene or benzene. This reaction may be typically conducted under reflux conditions, more generally from about 50° C. and 150° C. The product thus formed may be isolated by basifying an acidic aqueous solution of the salt form of the product and extracting the aqueous solution with a suitable water immiscible solvent. The resulting residue following evaporation can then be further purified if desired.

The 1-alkyl-4-methyl-4-(3-alkoxyphenyl) tetrahydropyridine derivatives may be prepared by a metalloenamine alkylation. This reaction is preferably conducted with n-butyllithium in tetrahydrofuran (THF) under an inert atmosphere, such as nitrogen or argon. Generally, a slight excess of n-butyllithium may be added to a stirring solution of the 1-alkyl-4-(3-alkoxyphenyl)-tetrahydropyridine in THF cooled to a temperature in the range of from about −50° C. to about 0° C., more preferably from about −20° C. to −10° C. This mixture may be stirred for approximately 10 to 30 minutes followed by the addition of approximately from 1.0 to 1.5 equivalents of methyl halide to the solution while maintaining the temperature of the reaction mixture below 0° C. After about 5 to 60 minutes, water may be added to the reaction mixture and the organic phase may be collected. The product can be purified according to standard procedures, but the crude product is preferably purified by either distilling it under vacuum or slurrying it in a mixture of hexane:ethyl acetate (65:35, v:v) and silica gel for about two hours. According to the latter procedure, the product may be then isolated by filtration followed by evaporating the filtrate under reduced pressure.

The next step in the process may involve the application of the Mannich reaction of aminomethylation to non-conjugated, endocyclic enamines. This reaction is preferably carried out by combining from about 1.2 to 2.0 equivalents of aqueous formaldehyde and about 1.3 to 2.0 equivalents of a suitable secondary amine in a suitable solvent. While water may be the preferred solvent, other non-nucleophilic solvents, such as acetone and acetonitrile can also be employed in this reaction. The pH of this solution may be adjusted to approximately 3.0 to 4.0 with an acid that provides a non-nucleophilic anion. Examples of such acids include sulfuric acid, the sulfonic acids such as methanesulfonic acid and p-toluenesulfonic acid, phosphoric acid, and tetrafluoroboric acid, with sulfuric acid being preferred. To this solution may be added one equivalent of a 1-alkyl-4-methyl-4-(3-alkoxyphenyl)tetrahydropyridine, typically dissolved in aqueous sulfuric acid, and the pH of the solution may be readjusted with the non-nucleophilic acid or a suitable secondary amine. The pH is preferably maintained in the range of from about 1.0 to 5.0, with a pH of about 3.0 to 3.5 being more preferred during the reaction. The reaction is substantially complete after about 1 to 4 hours, more typically about 2 hours, when conducted at a temperature in the range of from about 50° C. to about 80° C., more preferably about 70° C. The reaction may then be cooled to approximately 30° C., and added to a sodium hydroxide solution. This solution may then be extracted with a water immiscible organic solvent, such as hexane or ethyl acetate, and the organic phase, following thorough washing with water to remove any residual formaldehyde, may be evaporated to dryness under reduced pressure.

The next step of the process may involve the catalytic hydrogenation of the prepared 1-alkyl-4-methyl-4-(3-alkoxyphenyl)-3-tetrahydropyridinemethanamine to the corresponding trans-1-alkyl-3,4-dimethyl-4-(3-alkoxyphenyl) piperidine. This reaction actually occurs in two steps. The first step is the hydrogenolysis reaction wherein the exo C—N bond is reductively cleaved to generate the 3-methyltetrahydropyridine. In the second step, the 2,3-double bond in the tetrahydropyridine ring is reduced to afford the desired piperidine ring.

Reduction of the enamine double bond introduced the crucial relative stereochemistry at the 3 and 4 carbon atoms of the piperidine ring. The reduction generally does not occur with complete stereoselectivity. The catalysts employed in the process may be chosen from among the various palladium and preferably platinum catalysts.

The catalytic hydrogenation step of the process is preferably conducted in an acidic reaction medium. Suitable solvents for use in the process include the alcohols, such as methanol or ethanol, as well as ethyl acetate, tetrahydrofuran, toluene, hexane, and the like.

Proper stereochemical outcome may be dependent on the quantity of catalyst employed. The quantity of catalyst required to produce the desired stereochemical result may be dependent upon the purity of the starting materials in regard to the presence or absence of various catalyst poisons.

The hydrogen pressure in the reaction vessel may not be critical but can be in the range of from about 5 to 200 psi. Concentration of the starting material by volume is preferably around 20 mL of liquid per gram of starting material, although an increased or decreased concentration of the starting material can also be employed. Under the conditions specified herein, the length of time for the catalytic hydrogenation may not be critical because of the inability for over-reduction of the molecule. While the reaction can continue for up to 24 hours or longer, it may not be necessary to continue the reduction conditions after the uptake of the theoretical two moles of hydrogen. The product may then be isolated by filtering the reaction mixture for example through infusorial earth, and evaporating the filtrate to dryness under reduced pressure. Further purification of the product thus isolated may not be necessary and preferably the diastereomeric mixture may be carried directly on to the following reaction.

The alkyl substituent may be removed from the 1-position of the piperidine ring by standard dealkylation procedures. Preferably, a chloroformate derivative, especially the vinyl or phenyl derivatives, may be employed and removed with acid. Next, the prepared alkoxy compound may be dealkylated to the corresponding phenol. This reaction may be generally carried out by reacting the compound in a 48% aqueous hydrobromic acid solution. This reaction may be substantially complete after about 30 minutes to 24 hours when conducted at a temperature of from about 50° C. to about 150° C., more preferably at the reflux temperature of the reaction mixture. The mixture may then be worked up by cooling the solution, followed by neutralization with base to an approximate pH of 8. This aqueous solution may be extracted with a water immiscible organic solvent. The residue following evaporation of the organic phase may then be used directly in the following step.

The compounds employed as starting materials to the compounds of the invention can also be prepared by brominating the 1-alkyl-4-methyl-4-(3-alkoxyphenyl)-3-tetrahydropyridinemethanamine at the 3-position, lithiating the bromo compound thus prepared, and reacting the lithiated intermediate with a methylhalide, such as methyl bromide to provide the corresponding 1-alkyl-3,4-dimethyl-4-(3-alkoxyphenyl)tetrahydropyridinemethanamine. This compound may then be reduced and converted to the starting material as indicated above.

As noted above, the compounds of the present invention can exist as the individual stereoisomers. Preferably reaction conditions are adjusted as disclosed in U.S. Pat. No. 4,581, 456 or as set forth in Example 1 of U.S. Pat. No. 5,250,542 to be substantially stereoselective and provide a racemic mixture of essentially two enantiomers. These enantiomers may then be resolved. A procedure which may be employed to prepare the resolved starting materials used in the synthesis of these compounds includes treating a racemic mixture of alkyl-3,4-dimethyl-4-(3-alkoxyphenyl)piperidine with either (+)- or (−)-ditoluoyl tartaric acid to provide the resolved intermediate. This compound may then be dealkylated at the 1-position with vinyl chloroformate and finally converted to the desired 4-(3-hydroxyphenyl)piperidine isomer.

As will be understood by those skilled in the art, the individual enantiomers of the invention can also be isolated with either (+) or (−) dibenzoyl tartaric acid, as desired, from the corresponding racemic mixture of the compounds of the invention. Preferably the (+)-trans enantiomer is obtained.

Although the (+)trans-3,4 stereoisomer is preferred, all of the possible stereoiosmers of the compounds described herein are within the contemplated scope of the present invention. Racemic mixtures of the stereoisomers as well as the substantially pure stereoisomers are within the scope of the invention. The term "substantially pure", as used herein, refers to at least about 90 mole percent, more preferably at least about 95 mole percent and most preferably at least about 98 mole percent of the desired stereoisomer is present relative to other possible stereoisomers.

Intermediates can be prepared by reacting a 3,4-alkyl-substituted-4-(3-hydroxyphenyl)piperidine with a compound of the formula LCH$_2$(CH$_2$)$_{n-1}$CHR$^3$C(O)E where L is a leaving group such as chlorine, bromine or iodine, E is a carboxylic acid, ester or amide, and R$^3$ and n are as defined hereinabove. Preferably L may be chlorine and the reaction is carried out in the presence of a base to alkylate the piperidine nitrogen. For example 4-chloro-2-cyclohexylbutanoic acid, ethyl ester can be contacted with (3R,4R)-4-(3-hydroxyphenyl)-3,4-dimethylpiperidine to provide 4-[(3R,4R)-4-(3-hydroxyphenyl)-3,4-dimethyl-1-piperidine]butanoic acid, ethyl ester. Although the ester of the carboxylic acid may be preferred, the free acid itself or an amide of the carboxylic acid may be used.

In alternative synthesis, the substituted piperidine can be contacted with a methylene alkyl ester to alkylate the piperidine nitrogen. For example, 2-methylene-3-phenylproponic acid, ethyl ester can be contacted with a desired piperidine to provide 2-benzyl-3-piperidinepropanoic acid ethyl ester.

Another synthetic route can involve the reaction of a substituted piperidine with a haloalkylnitrile. The nitrile group of the resulting piperidine alkylnitrile can be hydrolyzed to the corresponding carboxylic acid.

With each of the synthetic routes, the resulting ester or carboxylic acid can be reacted with an amine or alcohol to provide modified chemical structures. In the preparation of amides, the piperidine-carboxylic acid or -carboxylic acid ester may be reacted with an amine in the presence of a coupling agent such as dicyclohexylcarbodiimide, boric acid, borane-trimethylamine, and the like. Esters can be prepared by contacting the piperidine-carboxylic acid with the appropriate alcohol in the presence of a coupling agent such as p-toluenesulfonic acid, boron trifluoride etherate or N,N'-carbonyldiimidazole. Alternatively, the piperidine-carboxylic acid chloride can be prepared using a reagent such as thionyl chloride, phosphorus trichloride, phosphorus pentachloride and the like. This acyl chloride can be reacted with the appropriate amine or alcohol to provide the corresponding amide or ester.

Opium alkaloid derivatives according to the present invention may be synthesized employing methods taught, for example, in U.S. Pat. Nos. 4,730,048 and 4,806,556, the disclosures of which are hereby incorporated herein by reference in their entireties. For example, opium alkaloid derivatives of formula (III) may be prepared by attaching hydrophilic, ionizable moieties R' and R" to the 6-amino group of naltrexamine (formula (III) where R is (cyclopropyl)methyl, Z is OH and R' is H) or oxymorphamine (formula (III) where R is CH$_3$, Z is OH and R' is H). The opium alkaloid derivatives of formula IV may be prepared by converting the 6-keto-group of oxymorphone (formula (VI) where R is CH$_3$ and Z is OH) or naltrexone (formula (VI) where R is (cyclopropyl)methyl and Z is OH) to the ionizable, hydrophilic group (R"N=) by a Schiff base reaction with a suitable amino-compound.

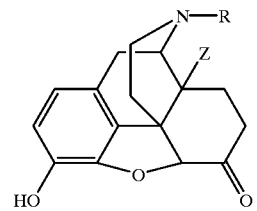

VI

In a similar fashion, deoxy-opiates of formulae (III) and (IV) wherein Z is hydrogen may be prepared from readily available starting materials.

The compounds of formula (V) may be synthesized employing methods taught, for example, in U.S. Pat. No. 3,723,440, the disclosures of which are hereby incorporated herein by reference in their entirety.

The compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents.

The compounds are preferably combined with a pharmaceutical carrier selected on the basis of the chosen route of administration and standard pharmaceutical practice as described, for example, in Remington's Pharmaceutical Sciences (Mack Pub. Co., Easton, Pa., 1980), the disclosures of which are hereby incorporated herein by reference, in their entirety.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges therein. Alternatively, the therapeutic human dosage may be from about 0.4 mg to about 10 g or higher, and may be administered in several different dosage units from once to several times a day. Generally speaking, oral administration may require higher dosages.

Compounds for use in the methods of the present invention, including piperidine-N-alkylcarboxylate compounds of formula (I), and particularly the compound of formula (II), have been characterized in opioid receptor binding assays and show preferential binding to mu opioid receptors. Studies in isolated tissues (guinea pig ileum and mouse vas deferens) have shown that these compounds may act as antagonists with no measurable agonist activity. Studies in animals have demonstrated that the present compounds may reverse constipation in morphine-dependent mice when administered orally or parenterally at very low doses, and do not block the analgesic actions of morphine unless given in hundred-fold or higher doses. Collectively, the data indicate that the compounds described herein may have a very high degree of peripheral selectivity. See, e.g., Zimmerman, D. M., et al., *Drugs of the Future,* 1994, 19(12), 1078–1083.

The invention is further described in the following example. The example, which is an actual example, is for illustrative purposes only, and is not to be construed as limiting the appended claims.

EXAMPLE

This example is directed to in vivo experiments in humans which demonstrate the effectiveness of the methods of the present invention.

Figure 2:
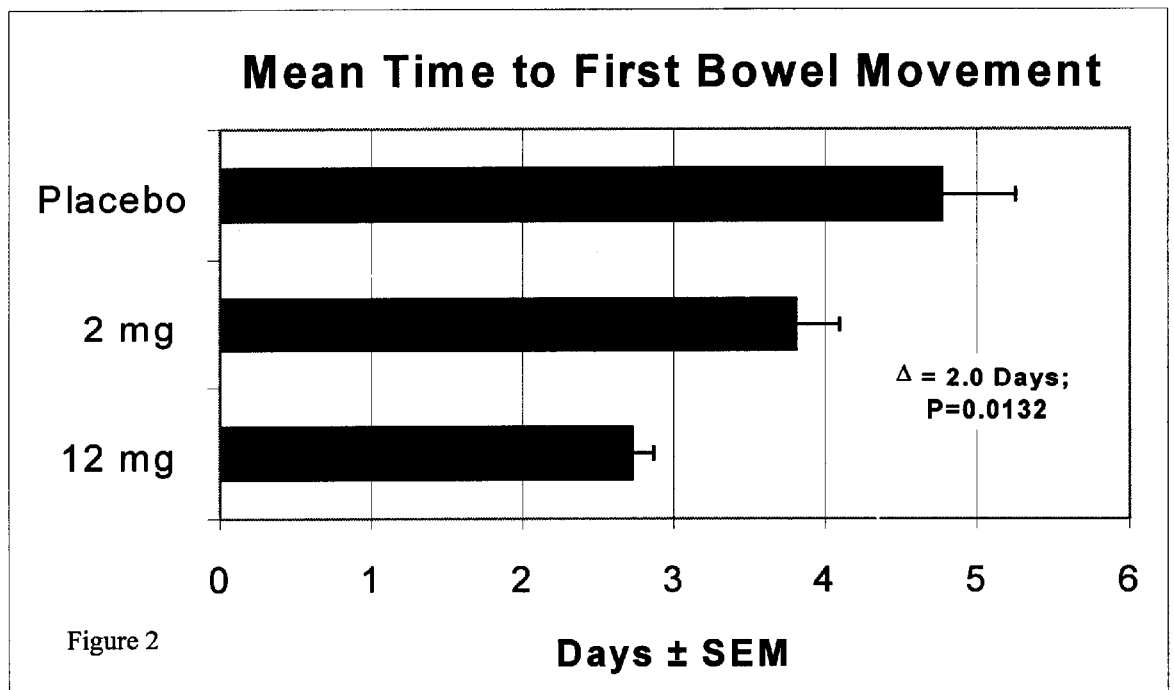
Figure 3:
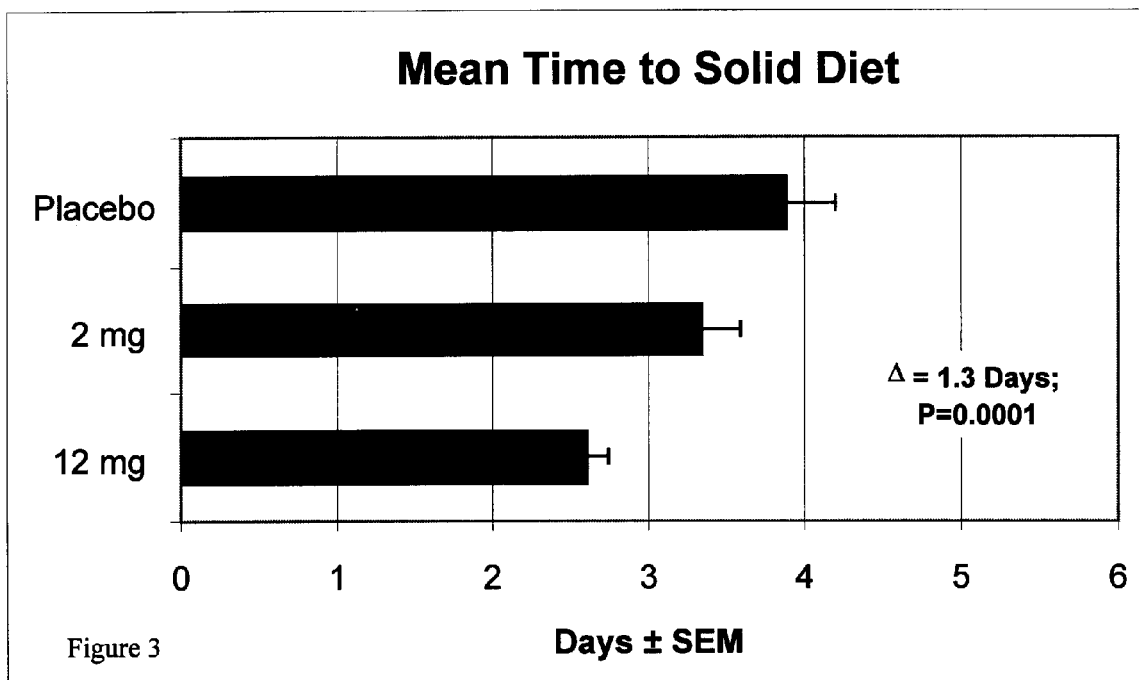
Figure 4:
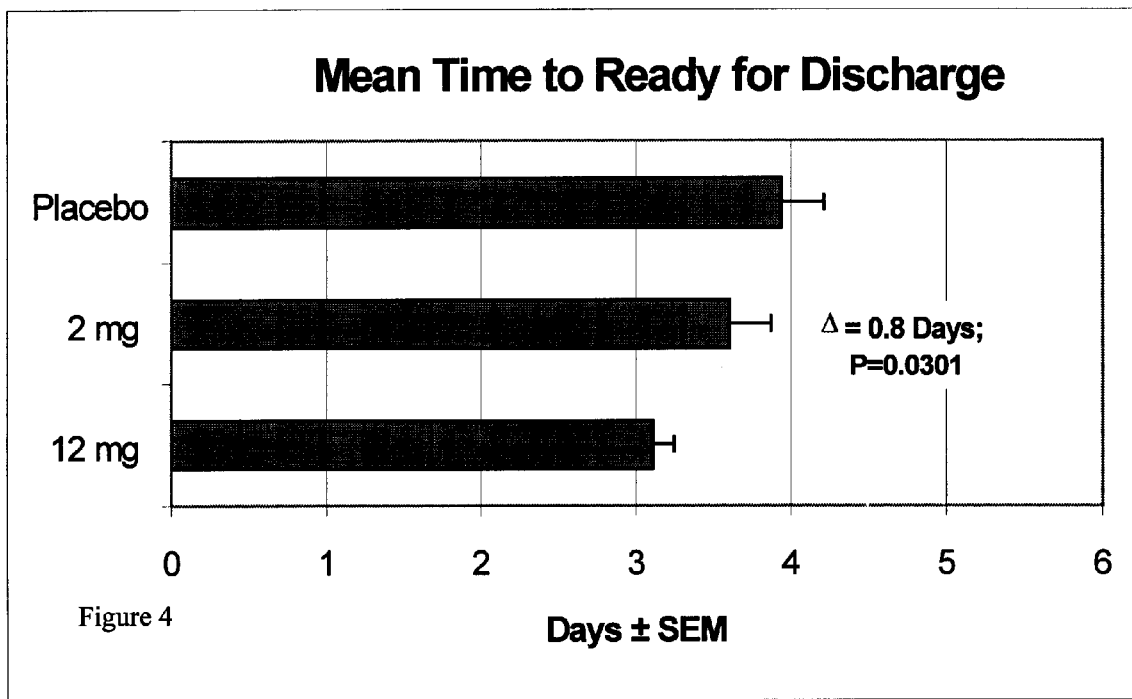
Figure 5:
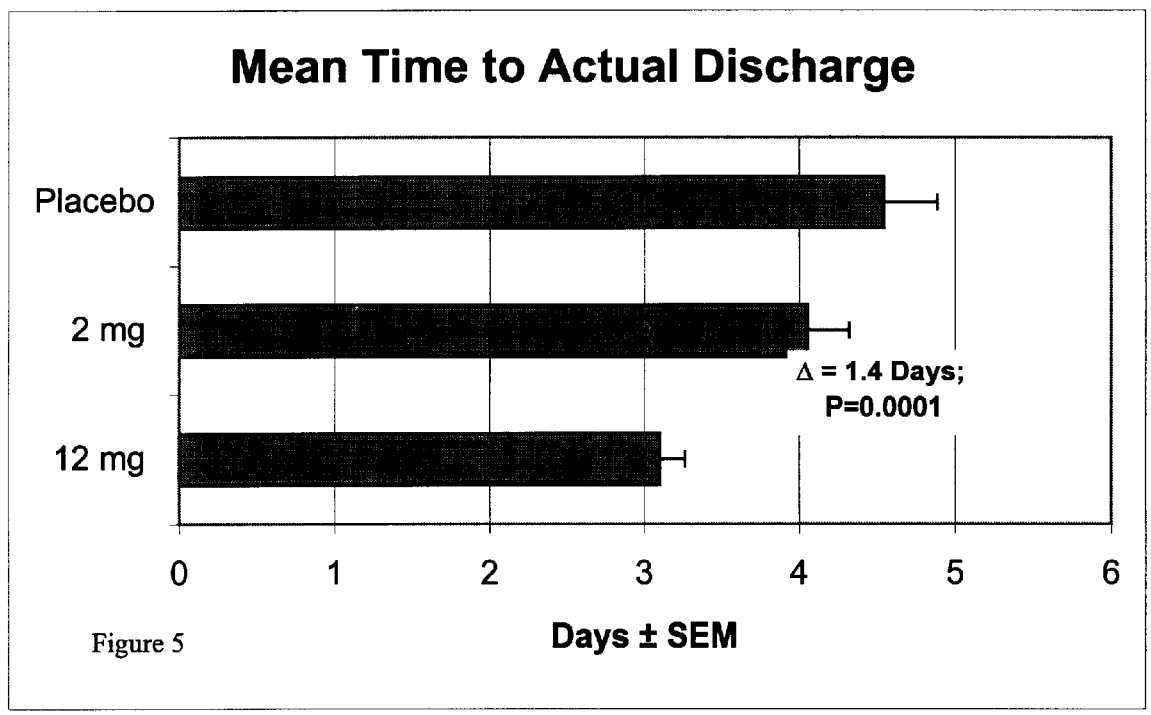

A 78 patient Phase II clinical study was conducted which compared two doses (2 mg and 12 mg) of the compound of formula (II) versus placebo in patients undergoing partial colectomy or simple or radical hysterectomy surgical procedures. The results of this study are set forth in the following Tables 1 to 4 and are depicted graphically in FIGS. 1 to 5.

TABLE 1

MEAN TIME TO FIRST FLATUS

| Dosage | Days | SEM (days) | Hours |
|---|---|---|---|
| 12 mg | 2.23 | 0.151 | 53.438 |
| 2 mg | 2.62 | 0.192 | 62.967 |
| Placebo | 2.86 | 0.275 | 68.675 |

Δ = 0.63

TABLE 2

MEAN TIME TO FIRST BOWEL MOVEMENT

| Dosage | Days | SEM (days) | Hours |
|---|---|---|---|
| 12 mg | 2.72 | 0.144 | 65.374 |
| 2 mg | 3.81 | 0.288 | 91.407 |
| Placebo | 4.77 | 0.488 | 114.406 |

Δ = 2.04

TABLE 3

MEAN TIME TO SOLID DIET

| Dosage | Days | SEM (days) | Hours |
|---|---|---|---|
| 12 mg | 2.60 | 0.139 | 62.515 |
| 2 mg | 3.35 | 0.247 | 80.298 |
| Placebo | 3.89 | 0.315 | 93.269 |

Δ = 1.28

TABLE 4

MEAN TIME TO READY TO DISCHARGE

| Dosage | Days | SEM (days) | Hours |
|---|---|---|---|
| 12 mg | 3.11 | 0.137 | 74.657 |
| 2 mg | 3.61 | 0.266 | 86.565 |
| Placebo | 3.94 | 0.277 | 94.536 |

Δ = 0.83

TABLE 5

MEAN TIME TO ACTUAL DISCHARGE

| Dosage | Days | SEM (days) | HOURS |
|---|---|---|---|
| 12 mg | 3.10 | 0.163 | 74.404 |
| 2 mg | 4.05 | 0.267 | 97.281 |
| Placebo | 4.54 | 0.344 | 109.071 |

Δ = 1.44

An analysis of the data in Tables 1 to 5 and FIGS. 1 to 5 shows a dose-dependent effect and that patients receiving a higher dose of the compound of formula (II) experienced shorter times to the following: (i) time to first flatus (P<0.04) (see Table 1 and FIG. 1); (ii) time to first bowel movement (P<0.02) (see Table 2 and FIG. 2); (iii) time to solid diet (P=0.0001) (see Table 3 and FIG. 3); (iv) time to being ready for discharge from the hospital (P<0.04) (see Table 4 and FIG. 4); and (v) time to discharge from the hospital (P=0.0001) (see Table 5 and FIG. 5). The time to first flatus was reduced by 15 hours; all other measures were reduced by 24 hours or more. No patients experienced serious adverse side effects in this trial that were judged by the clinical investigator to be related to the activity of the compound of formula (II). The patients treated with the higher dose of the compound of formula (II) actually experienced fewer overall adverse effects than the patients in the placebo-treated group since compound (II) blocked the adverse gastrointestinal effects of morphine or other narcotic analgesics that were used for post-surgical pain relief. In particular, none of the patients receiving the higher dose of the compound of formula (II) experienced post-surgical vomiting compared to 23% in the placebo control group (P<0.03). Twenty seven percent of the patients receiving the higher dose of compound (II) experienced clinically relevant post-surgical nausea compared to 63% of the placebo control group (P=0.003). The compound of formula (II) also did not reduce the beneficial analgesic effects of systemic narcotics used in this trial. These results demonstrate that the compound of formula (II) may speed recovery of normal bowel function after surgery.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A method of treating or preventing ileus comprising administering to a patient an effective amount of a compound of the following formula (I):

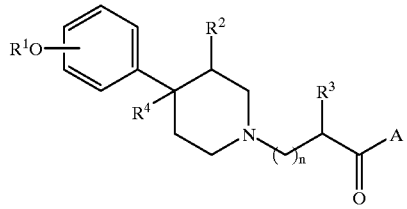

wherein:

$R^1$ is hydrogen or alkyl;

$R^2$ is hydrogen, alkyl or alkenyl;

$R^3$ is hydrogen, alkyl, alkenyl, aryl, cycloalkyl, cycloalkenyl, cycloalkyl-substituted alkyl, cycloalkenyl-substituted alkyl or aryl-substituted alkyl;

$R^4$ is hydrogen, alkyl or alkenyl;

A is $OR^5$ or $NR^6R^7$; wherein:

$R^5$ is hydrogen, alkyl, alkenyl, cycloalkyl, cycloalkenyl, cycloalkyl-substituted alkyl, cycloalkenyl-substituted alkyl, or aryl-substituted alkyl;

$R^6$ is hydrogen or alkyl;

$R^7$ is hydrogen, alkyl, alkenyl, cycloalkyl, aryl, cycloalkyl-substituted alkyl, cycloalkenyl, cycloalkenyl-substituted alkyl, aryl-substituted alkyl, aryl-substituted alkyl, or alkylene substitued B or, together with the nitrogen atom to which they are attached, $R^6$ and $R^7$ form a heterocyclic ring selected from pyrrole and piperidine;

B is

[structures: oxadiazole with R²¹, and tetrazole]

C(=O)W or NR⁸R⁹; wherein;

R⁸ is hydrogen or alkyl;

R⁹ is hydrogen, alkyl, alkenyl, cycloalkyl-substituted alkyl, cycloalkyl, cycloalkenyl, cycloalkenyl-substituted alkyl, aryl or aryl-substituted alkyl or, together with the nitrogen atom to which they are attached, R⁸ and R⁹ form a heterocyclic ring selected from pyrrole and piperidine;

W is OR¹⁰, NR¹¹R¹², or OE; wherein

R¹⁰ is hydrogen, alkyl, alkenyl, cycloalkyl, cycloalkenyl, cycloalkyl-substituted alkyl, cycloalkenyl-substituted alkyl, or aryl-substituted alkyl;

R¹¹ is hydrogen or alkyl;

R¹² is hydrogen, alkyl, alkenyl, aryl, cycloalkyl, cycloalkenyl, cycloalkyl-substituted alkyl, cycloalkenyl-substituted alkyl, aryl-substituted alkyl or alkylene substituted C(=O)Y or, together with the nitrogen atom to which they are attached, R¹¹ and R¹² form a heterocyclic ring selected from pyrrole and piperidine;

E is

[structure: 1,3-dioxol-2-one with CH₂— and CH₃]

alkylene substituted (C=O)D, or —R¹³OC(=O)R¹⁴; wherein

R¹³ is alkyl substituted alkylene;

R¹⁴ is alkyl;

D is OR¹⁵ or NR¹⁶R¹⁷ wherein:

R¹⁵ is hydrogen, alkyl, alkenyl, cycloalkyl, cycloalkenyl, cycloalkyl-substituted alkyl, cycloalkenyl-substituted alkyl, or aryl-substituted alkyl;

R¹⁶ is hydrogen, alkyl, alkenyl, aryl, aryl-substituted alkyl, cycloalkyl, cycloalkenyl, cycloalkyl-substituted alkyl or cycloalkenyl-substituted alkyl;

R¹⁷ is hydrogen or alkyl or, together with the nitrogen atom to which they are attached, R¹⁶ and R¹⁷ form a heterocyclic ring selected from pyrrole and piperidine;

Y is OR¹⁸ or NR¹⁹R²⁰; wherein:

R¹⁸ is hydrogen, alkyl, alkenyl, cycloalkyl, cycloalkenyl, cycloalkyl-substituted alkyl, cycloalkenyl-substituted alkyl, or aryl-substituted alkyl;

R¹⁹ is hydrogen or alkyl;

R²⁰ is hydrogen, alkyl, alkenyl, aryl, cycloalkyl, cycloalkenyl, cycloalkyl-substituted alkyl, cycloalkenyl-substituted alkyl, or aryl-substituted alkyl or, together with the nitrogen atom to which they are attached, R¹⁹ and R²⁰ form a heterocyclic ring selected from pyrrole and piperidine;

R²¹ is hydrogen or alkyl; and n is 0 to 4;

or a stereoisomer, prodrug, or pharmaceutically acceptable salt, hydrate or N-oxide thereof.

2. A method according to claim 1 wherein the compound of formula (I) is a trans 3,4-isomer.

3. A method according to claim 1 wherein R¹ is hydrogen; R² is alkyl; n is 1 or 2; R³ is benzyl, phenyl, cyclohexyl, or cyclohexylmethyl; and R⁴ is alkyl.

4. A method according to claim 3 wherein A is OR⁵ in which R⁵ is hydrogen or alkyl.

5. A method according to claim 3 wherein A is NR⁶R⁷ in which R⁶ is hydrogen and R⁷ is alkylene substituted B wherein B is C(O)W.

6. A method according to claim 5 wherein R⁷ is (CH₂)$_q$—B in which q is about 1 to about 3; and W is OR¹⁰ in which R¹⁰ is hydrogen, alkyl, phenyl-substituted alkyl, cycloalkyl or cycloalkyl-substituted alkyl.

7. A method according to claim 5 wherein W is NR¹¹R¹² in which R¹¹ is hydrogen or alkyl, and R¹² is hydrogen, alkyl or alkylene substituted C(=O)Y.

8. A method according to claim 7 wherein R¹² is (CH₂)$_m$C(O)Y in which m is 1 to 3 and Y is OR¹⁸ or NR¹⁹R²⁰ wherein R¹⁸, R¹⁹ and R²⁰ are independently hydrogen or alkyl.

9. A method according to claim 5 wherein W is OE in which E is CH₂C(=O)D wherein D is OR¹⁵ or NR¹⁶R¹⁷ in which R¹⁵ is hydrogen or alkyl, R¹⁶ is methyl or benzyl and R¹⁷ is hydrogen.

10. A method according to claim 5 wherein W is OE in which E is R¹³OC(=O)R¹⁴, wherein R¹³ is —CH(CH₃)— or —CH(CH₂CH₃)— and R¹⁴ is alkyl.

11. A method according to claim 1 wherein the configuration at positions 3 and 4 of the piperidine ring is each R.

12. A method according to claim 1 wherein said compound is selected from the group consisting of Q—CH₂CH(CH₂(C₆H₅))C(O)OH, Q—CH₂CH₂CH(C₆H₅)C(O)NHCH₂C(O)OCH₂CH₃, Q—CH₂CH₂CH(C₆H₅)C(O)NHCH₂C(O)OH, Q—CH₂CH₂CH(C₆H₅)C(O)NHCH₂C(O)NHCH₃, Q—CH₂CH₂CH(C₆H₅)C(O)NHCH₂C(O)NHCH₂CH₃, G—NH(CH₂)₂C(O)NH₂, G—NH(CH₂)₂C(O)NHCH₃, G—NHCH₂C(O)NH₂, G—NHCH₂C(O)NHCH₃, G—NHCH₃C(O)NHCH₂CH₃, G—NH(CH₂)₃C(O)OCH₂CH₃, G—NH(CH₂)₃C(O)NHCH₃, G—NH(CH₂)₂C(O)OH, G—NH(CH₂)₃C(O)OH, Q—CH₂CH(CH₂(C₆H₁₁))C(O)NHCH₂C(O)OH, Q—CH₂CH(CH₂(C₆H₁₁))C(O)NH(CH₂)₂C(O)OH, Q—CH₂CH(CH₂(C₆H₁₁))C(O)NH(CH₂)₂C(O)NH₂, Z—NHCH₂C(O)OCH₂CH₃, Z—NHCH₂C(O)OH, Z—NHCH₂C(O)NH₂, Z—NHCH₂C(O)N(CH₃)₂, Z—NHCH₂C(O)NHCH(CH₃)₂, Z—NHCH₂C(O)OCH₂CH(CH₃)₂, Z—NH(CH₂)₂C(O)OCH₂(C₆H₅), Z—NH(CH₂C(O)OH, Z—NH(CH₂)₂C(O)NHCH₂CH₃, Z—NH(CH₂)₃C(O)NHCH₃, Z—NHCH₂C(O)NHCH₂C(O)OH, Z—NHCH₂C(O)OCH₂C(O)OCH₃, Z—NHCH₂C(O)O(CH₂)₄CH₃, Z—NHCH₂C(O)OCH₂C(O)NHCH₃, Z—NHCH₂C(O)O—(4-methoxycyclohexyl), Z—NHCH₂C(O)OCH₂C(O)NHCH₂(C₆H₅) or Z—NHCH₂C(O)OCH(CH₃)OC(O)CH₃; wherein:

Q represents

[structure: trans-3,4-dimethyl piperidine with 3-hydroxyphenyl substituent, labeled trans-3,4-dimethyl, HO on phenyl, H₃C groups, N—]

G represents

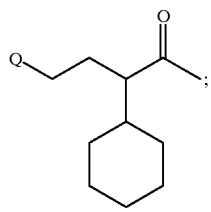

and Z represents

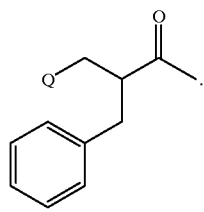

13. A method according to claim 12 wherein said compound is Q-CH$_2$CH(CH$_2$(C$_6$H$_5$))C(O)OH.

14. A method according to claim 13 wherein said compound is (3R, 4R, S)- Q-CH$_2$CH(CH$_2$(C$_6$H$_5$))C(O)OH.

15. A method according to claim 12 wherein said compound is selected from the group consisting of (3R,4R,S)-Z—NHCH$_2$C(O)OCH$_2$CH(CH$_3$)$_2$, (+)-Z—NHCH$_2$C(O)OH, (−)-Z—NHCH$_2$C(O)OH, (3R,4R,R)-Z—NHCH$_2$C(O)—OCH$_2$CH(CH$_3$)$_2$, (3S,4S,S)-Z—NHCH$_2$C(O)OCH$_2$CH(CH$_3$)$_2$, (3S,4S,R)-Z—NHCH$_2$C(O)OCH$_2$CH(CH$_3$)$_2$, (3R,4R)-Z—NHCH$_2$C(O)NHCH$_2$(C$_6$H$_5$) or (3R, 4R)-G—NH(CH$_2$)$_3$C(O)OH.

16. A method according to claim 15 wherein said compound is selected from the group consisting of (+)-Z—NHCH$_2$C(O)OH and (−)-Z—NHCH$_2$C(O)OH.

17. A method according to claim 16 wherein said compound is (+)-Z—NHCH$_2$C(O)OH.

18. A method according to claim 1 wherein said compound is a substantially pure stereoisomer.

19. A method according to claim 1 wherein the ileus is selected from the group consisting of postsurgical ileus and postpartum ileus.

20. A method according to claim 19 wherein the ileus is postsurgical ileus.

21. A method according to claim 20 wherein said postsurgical ileus is postsurgical paralytic ileus.

22. A method according to claim 1 wherein the compound of formula (I) is a peripheral mu opioid antagonist compound.

23. A method according to claim 1 further comprising administering an opiate or an opioid to said patient.

24. A method according to claim 23 wherein said opiate or opioid comprises an opioid analgesic.

25. A method according to claim 24 wherein said opioid analgesic comprises a mu opioid agonist.

26. A method according to claim 1 further comprising administering to said patient a compound which slows gut motility.

* * * * *

UNITED STATES PATENT AND TRADEMARK OFFICE
CERTIFICATE OF CORRECTION

PATENT NO. : 6,469,030 B2
DATED : October 22, 2002
INVENTOR(S) : John J. Farrar et al.

It is certified that error appears in the above-identified patent and that said Letters Patent is hereby corrected as shown below:

Title page,
Item [56], References Cited, OTHER PUBLICATIONS, "Bergasa" reference, after "1404-1412" insert -- (abstract only) --; "Moerman" reference, delete "mausea" and insert -- nausea --; "Roger" reference, after "31-35" insert -- (abstract only) --;

Column 12,
Line 60, delete "alky" and insert therefore -- alkyl --;

Column 17,
Line 33, delete "(I)" and insert therefore -- (IV) --;

Column 30,
Lines 45 and 46, delete "($C_6H_{11}$)" and insert -- ($C_6H_{11}$)) --.

Signed and Sealed this

Twenty-third Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,469,030 B2
DATED : October 22, 2002
INVENTOR(S) : Farrar et al.

It is certified that error appears in the above-identified patent and that said Letters Patent is hereby corrected as shown below:

Title page,
Item [62], Related U.S. Application Data, please delete "Continuation-in-part of application No. 09/450,920, filed on Nov. 29, 1999, now abandoned."
and replace with -- This application claims benefit under 35 U.S.C 119(e) to U.S. Provisional Application Serial No. 60/287,560, filed November 29, 1999. --; and and please delete "This application is a continuation-in-part of application Ser. No. 09/450,920, filed Nov. 29, 1999, now abandoned."

Column 1,
Line 9, after the word "under", please insert -- 35 --.
Line 10, after "Ser.No. 60/28 7,560", please insert -- , filed Nov. 29, 1999. --

Signed and Sealed this

Tenth Day of August, 2004

JON W. DUDAS
*Acting Director of the United States Patent and Trademark Office*